United States Patent [19]

Lampotang et al.

[11] Patent Number: 5,769,641
[45] Date of Patent: Jun. 23, 1998

[54] APPARATUS AND METHOD FOR SYNCHRONIZING CARDIAC RHYTHM RELATED EVENTS

[75] Inventors: Samsun Lampotang; Willem L. van Meurs; Michael L. Good; Joachim S. Gravenstein; Ronald G. Carovano, all of Gainesville, Fla.

[73] Assignee: University of Florida Research Foundation, Inc., Gainsville, Fla.

[21] Appl. No.: 767,947

[22] Filed: Dec. 17, 1996

Related U.S. Application Data

[60] Division of Ser. No. 188,383, Jan. 27, 1994, Pat. No. 5,584,701, which is a continuation-in-part of Ser. No. 882,467, May 13, 1992, Pat. No. 5,391,081.

[51] Int. Cl.⁶ .................................................. G09B 23/28
[52] U.S. Cl. ............................................ 434/272; 434/262
[58] Field of Search .................................... 434/262, 265, 434/266, 267, 268, 272, 275; 128/774

[56] References Cited

U.S. PATENT DOCUMENTS

| | | |
|---|---|---|
| 3,520,071 | 7/1970 | Abrahamson et al. . |
| 3,661,052 | 5/1972 | Lucien et al. . |
| 3,808,706 | 5/1974 | Mosley et al. . |
| 3,888,020 | 6/1975 | Krause ..................... 434/266 |
| 4,167,070 | 9/1979 | Orden . |
| 4,561,851 | 12/1985 | Ferreira et al. . |
| 4,570,640 | 2/1986 | Barsa . |
| 4,878,388 | 11/1989 | Loughlin et al. . |
| 4,907,973 | 3/1990 | Hon . |
| 5,385,474 | 1/1995 | Brindle ..................... 434/267 |
| 5,403,192 | 4/1995 | Kleinwaks et al. . |
| 5,509,810 | 4/1996 | Schertz et al. .......... 434/262 |

OTHER PUBLICATIONS

M.L. Good, M.D., and J. S. Gravenstein, M.D., *Anesthesia Simulators and Training Device*, International Anesthesiology Clinics 27:161–164 (1989).

Good, et al., *Hybrid Lung Model for Use in Anesthesia Research and Education Anesthesiology*. Hybrid Lung Model for Use in Anesthesia Research and Education, 71:982–984 (1989).

D.M. Gaba, M.D. and A. DeAnda, *A Comprehensive Anesthesia Simulation Environment: Re-creating the Operating Room for Research and Training*, Anesthesiology, 69:387–389 (1988).

M.L. Good,et al., *Critical Events Simulation for Training in Anesthesiology*, Journal of Clinical Monitoring, 4:140 (1988).

S. Lampotang, et al., *A lung model of carbon dioxide concentrations with mechanical or spontaneous ventilation*, Critical Care Medicine, 14:1055–1057, (1986).

S. Abrahamson, *Chapter 31: Human Simulation for Training in Anesthesiology*, Medical Engineering, pp. 370–374.

J. S. Densen, M.D. and S. Abrahamson, Ph.D., *A Computer–Controlled Pateint Simulator*, JAMA, 208:504–508, (1969).

Ross et al., *Servocontrolled Closed Circuit Anaesthesia: A method for the automatic controlof anaethesia produced by a volatile agent in oxygen*, British Journal of Anesthesia, 44:1053–1060 (1983).

*Primary Examiner*—John P. Leubecker
*Attorney, Agent, or Firm*—Needle & Rosenberg, PC

[57] ABSTRACT

An apparatus and method for synchronizing output devices related to a cardiac rhythm in real time in an integrated patient simulator during simulated medical surgery includes a manikin, at least one output device including devices for simulating a cardiac pulse and a radial pulse, a first computer associated with the patient simulator for generating an electric cardiac rhythm synchronizing pulse, a second computer for receiving the cardiac rhythm synchronizing pulse and generating a simulated response thereto, and a distributed processing network for transmitting the cardiac rhythm synchronizing pulse between the first computer and the second computer and for transmitting the simulated response between the second computer and the output device. In this way, a time offset to allow for simulated travel time or lag of the simulated cardiac pulse through the body can be added by the second computer where appropriate for certain subsystems or monitors associated with the patient simulator.

21 Claims, 7 Drawing Sheets

APPARATUS AND METHOD FOR SYNCHRONIZING CARDIAC RHYTHM RELATED EVENTS

CROSS-REFERENCE TO RELATED APPLICATION

This application is a divisional of Applicant's U.S. Ser. No. 08/188,383, filed Jan. 27, 1994, now U.S. Pat. No. 5,584,701, which, in turn, is a continuation-in-part of Applicant's U.S. Ser. No. 07/882,467, filed May 13, 1992, issued as U.S. Pat. No. 5,391,081, the contents of all of which are hereby incorporated by this reference.

BACKGROUND

1. Field of the Invention

This invention relates to an integrated patient simulator and methods of using the same. In particular, this invention discloses an improved patient simulator capable of realistically simulating nerve stimulation, lung movement, lung volume measurement and lung breathing noise, administration, detection, identification and quantification of medicaments and fluids introduced during simulated surgery, bronchial resistance, computer controllable compliances and also possessing an improved computational configuration, an electric cardiac synchronization pulse, audible heart and lung sounds, simulation of continuous blood gases, pulmonary artery (PA) catheter inflation detection, difficult airway, spontaneous breathing and other anesthesiological indications, and gas exchange via a mass-flow controller.

2. Background of the Invention

Currently, a new resident in medicine will receive a very limited duration of didactic teaching about the principles of particular medical procedures, such as anesthesia, before delivering care to his/her first real patient. The resident is then faced with a now and unfamiliar environment while shouldering the tremendous responsibility of caring for an ill and sometimes anesthetized patient. Similarly, experienced physicians who require continuing medical education, refresher courses (e.g., handling of rare ailments and situations) or familiarization with newly introduced and/or technologically sophisticated equipment or procedures do not have the opportunity for hands-on practice in a realistic environment, without risk to a patient. Of course, these undesirable situations also apply to other disciplines such as allied health care and veterinary medicine, for instance.

The patient simulator disclosed in U.S. patent application Ser. No. 07/882,467, now U.S. Pat. No. 5,391,081, addresses the above-mentioned deficiencies in medical, allied health care and veterinary education. The improved self-regulating full-scale patient simulator technology described herein comprises further embodiments of a patient simulator.

The lung portion of the integrated patient simulator disclosed herein consumes and/or produces gases including oxygen, carbon dioxide, nitrogen, nitrous oxide and volatile anesthetics. Under the control of a mathematical model of human physiology implemented on a computer, uptake and delivery of the above mentioned gases is computed by the uptake and delivery module of the physiological model. The computed uptake and delivery is then physically created by gas substitution in the hardware module for simulating gas exchange in the lung simulator portion of the patient simulator. The lung will also simulate spontaneous inspiration with computer control of tidal volume (VT), respiratory rate (RR) and functional residual capacity (FRC) and will also allow the simulation of a cough. In addition, the lung will exhibit the desired lung mechanics and gas exchange when mechanically or manually ventilated.

The patient simulator system of this invention has several components including lung mechanics (software and hardware); gas exchange (software and hardware); a physiologic model (software); cardiovascular; uptake and distribution; neuromuscular system; pharmacokinetics/pharmacodynamics; physiologic control models; and a unique linking of the different subsystems of the patient simulator so that the patient responds realistically to inputs from the trainee/student.

A major improvement of the lung/patient simulator is that it allows realistic action/reaction interplay between the actions of the trainee, responses of the simulated patient, data shown on the monitors and subsequent actions by the trainee. Another significant improvement that distinguishes the lung/patient simulator from similar systems is that its software and hardware are self-regulating. The present hybrid (mechanical and mathematical) lung model regulates itself regardless of type of gas (air, anesthetics, hypoxic, etc.) inhaled, and, surprisingly, even the blunting of physiological control mechanisms (e.g., ventilatory response to carbon dioxide) is self-regulated.

The present patient simulator is an integrated, self-regulating system. For instance, in a non-self-regulating system, an awkward input situation would invariably lead to physiologically implausible behavior from the system or such stimuli would result in an inability of the system to handle the input at all. A self-regulating system is more robust in the accommodation and simulation of unplanned events because it will still provide an appropriate response. Thus, self-regulation is highly desirable, yet glaringly absent from the prior art.

For instance, if the trainee accidently ventilates the lung with a hypoxic (lacking oxygen) gas mixture (e.g. pure argon gas), a conventional system may not be able to react appropriately. However, the present invention provides an integration of relevant systems such that, through self-regulation, appropriate simulated manifestations of hypoxia would be produced in the various output devices of the patient simulator, e.g. increased breathing rate and heart rate.

As another example, those skilled in the art are aware that increased $CO_2$ levels in the lung will cause hyperventilation. Hyperventilation results in lowering of $CO_2$ levels in the lungs due to washing away of the carbon dioxide. In a non-self-regulating patient simulator, increased lung $CO_2$ may or may not lead to increased ventilation. If no increase occurs, the reality of the simulation is decreased, thereby lessening the teaching value of the simulation.

Thus, it is clear that self-regulating systems hold clear advantages above non-self-regulating systems.

Furthermore, a means for adequately handling the injection of liquid anesthetic into the breathing circuit has been attempted by other researchers. The problems encountered in the prior art included (a) freezing of the location where the liquid anesthetic is introduced because of the heat of vaporization extracted from the surroundings as the liquid anesthetic evaporates, (b) pooling of the injected liquid through lack of heat to vaporize the liquid anesthetic and (c) uncontrolled evaporation of the anesthetic liquid from the syringe to the breathing circuit (i.e. the tubing or conduit assembly which physically connects the anesthesia machine or ventilator to the patient/manikin). The instant integrated patient simulator solves these problems by providing a means as usable not only in the simulation but in real life anesthesia applications.

A real life practitioner must be able to react to a patient who is undergoing a degree of bronchial restriction. Therefore, it is highly desirable for a patient simulator to be able to simulate bronchial resistance where the restriction of gas flow may be varied upon a continuum. Without manual intervention, such capability is lacking in the prior art systems.

In a full-scale patient simulator, it is necessary to be able to simulate changes in bronchial resistance. In a full-scale simulator using real gas flows, independent computer-controlled variable orifices (with maximum openings of 0.5" diameter) placed in the bronchi would allow simulation of changes in bronchial or airway resistance. No prior art devices (e.g., photographic camera iris diaphragms) were found which could simulate variable bronchial resistances in the relevant diameter range. Furthermore, a device capable of allowing a suction catheter to pass down the bronchus was preferable. Thus, the present invention could not use butterfly valves with an internal diameter of 0.5".

Another possible embodiment was a stepper motor actuated cam or lever that presses a flexible conduit closed. However, because the stepper motor would have needed to be overly large in order to provide the force necessary to maintain the flow area completely closed and capable of holding a pressure of 120 cm $H_2O$, one of the design specifications, it was highly desirable and necessary to design an alternative computer-controlled variable orifice device.

During simulation, it is preferable if the drugs and IV fluid administered by the trainee to the simulated patient are automatically sensed and input into the computer, rather than having to depend on the simulation instructor to recognize and manually enter the drug or IV fluid type, concentration and dose administered to the patient. Thus, in prior systems, the simulation instructor might be distracted and miss the administration of the drug or IV fluid by the student or might manually enter into the simulation controller the wrong type, concentration or dose of the drug or IV fluid.

In addition, the amount of drug and/or IV fluid administered by the student is a critical input to the physiological model of the patient because the response of the patient is dose- and volume-dependent. The amount of IV fluid dripped into the patient is also a parameter that needs to be quantified if the fluid balance of the simulated patient is to be correctly modelled. It does not appear that prior art system have contemplated a means for quantification of drug admired. As in drug identification, a system that will allow quantification of the amount of drug or IV fluid injected via an intravenous (IV) line without the need for a human observer is highly desirable.

U.S. patent application Ser. No. 07/882,467 disclosed and claimed one embodiment of distributed processing network for implementing the computer portions of the current patient simulator: a ring-shaped array of single-board computers (i.e., DACS PAN—Data Acquisition and Control System).

It has been found that a star configuration for a network of single board computers is more preferable. The extent of computational power and parallel processing required for simulating a patient's different physiological subsystems is facilitated by a distributed processing network. For example, one computer takes modulates the mechanical lung while another controls the palpable pulses. The ring network is less robust than a star network configuration because if one of the single board computers becomes non-functional, the entire network ceases to operate. In the star network configuration, the network will still function even if one of the computers on the network fails.

The realism of a simulation would be marred if the different signs or variables dependent on the cardiac rhythm were at different frequencies (e.g., an ECG heart rate of 70 beats per minute (bpm) but a pulse rate from the pulse oximeter of 90 bpm). A mechanism that allows synchronization of all cardiac related events is, therefore, highly desirable and necessary for a realistic patient simulator.

The realism of a patient simulator would also be compromised if the simulator lacked audible heart, lung and breathing sounds emanating from the appropriate portions of the simulator. In addition, spontaneous breathing is highly desirable and adds to the realism of the patient simulator.

In addition, a realistic patient simulator should be able to simulate the monitoring of continuous blood gases. Simulation of continuous blood gases monitoring is highly desirable in light of recent technological advances implementing such technology in the everyday practice of specialists. Furthermore, it is highly desirable that a patient simulator have a means for detecting pulmonary artery (PA) catheter inflation.

Also, it is desirable to have a patient simulator capable of simulating a difficult airway. Difficult airway may be caused by a number of factors, such as an allergic reaction. In a difficult airway situation, the patient's trachea closes and prevents the flow of air in and out of the patient's lungs. Thus blocked, it is not possible to insert through the trachea an endotracheal tube (ETT) for securing the airway. It is highly desirable to provide a patient simulator capable of simulating this potential complication so that a trainee may be taught the proper response techniques such as a cricothyrotomy.

In addition, a difficult airway is a potentially lethal incident which anesthesiologists and other practitioners will likely encounter in actual patients. The American Society of Anesthesiologists has declared that is essential for any anesthesiologist to know how to handle such a situation as one of his or her practice parameters. Thus, the patient simulator provides a risk-free way to assess whether a trainee has successfully learned how to handle a difficult airway.

It is also desirable to provide a patient simulator capable of efficient and realistic gas exchange. Although a previous embodiment of the patient simulator contained a gas exchange module, the current module differs in important ways. Most importantly, the patient simulator disclosed herein uses mass flow controllers instead of frequency modulated valves as in the previous embodiment. Modulated valves provided inaccurate control over the flow rate of the different gases. In addition, maximum flow rate was limited in the prior embodiment in an unrealistic fashion which resulted in an unrealistically small difference between inhaled and exhaled oxygen levels. Finally, the frequency modulated valves resulted in inconsistent signals transmitted to the capnogram (depiction of $CO_2$ level over time) which manifested themselves as ripples instead of straight lines, especially during plateau portions of the exhalation.

In addition, instead of a "copper kettle" Vernitrol vaporizer being used to introduce vaporized volatile anesthetic into the lung bellows, a syringe pump with a novel copper device is used in the present invention. In copper kettle systems, a carrier gas (generally $O_2$) is bubbled through a pool of liquid anesthetic contained in a solid copper vaporizer. The use of the syringe pump eliminates the necessity of using a carrier gas per se thus simplifying the behavior of the gas exchange subsystem in general.

Realistic simulation of gas exchange is necessary because it allows the use of real or modified medical gas analyzers such as those used in real operating rooms. Other simulators do not model gas exchange at all. Instead, other simulators in the art bleed $CO_2$ at variable rates into the bellows representing the simulated lungs. Thus, the simulators are incapable of simulating even the most rudimentary gases being exchanged such as oxygen. Nor are those systems capable of simulating the consumption or excretion of the amount of volatile anesthetics.

In addition, when an oxygen analyzer is used to sample the flow of gases into and out of a real patient's lung, exhaled oxygen will be notably lower than inhaled oxygen due to consumption in the patient's lungs. Unlike other simulators, the patient simulator of this invention is capable of realistically portraying to external monitoring equipment the differential between inspired and expired oxygen concentration. When other simulators are linked to an oxygen analyzer, the insiparatory and expiratory oxygen levels will be identical either indicating grave health problems to the patient or a serious breakdown in the realism of the simulation. Thus, the accurate modeling of gas exchange, as accomplished by the instant invention is highly desirable.

SUMMARY OF THE INVENTION

The present invention discloses a self-regulated lung in a manikin for use in real time in an integrated patient simulator during simulated medical procedures, comprising at least one bellows capable of receiving and expelling a gas, a means for actuating the bellows between expanded and contracted states depending upon a time- and event-based script, a computer model or a combination of a time- and event-based script and a computer model based on the physiological state of the patient simulator, at least one mass flow controller capable of directing the gas into the bellows when the bellows expands in volume, a fist conduit interconnecting the mass flow controller and the bellows, a vane pump capable of expelling the gas from the bellows when the bellows contracts in volume, and a second conduit interconnecting the bellows and the vane pump. In a preferred embodiment, the means for actuating the bellows between an expanded and a contracted state comprises a double acting piston attached to the bellows and a first constant pressure and a second variable pressure acting on respective sides of the double acting piston whereby varying the second variable pressure causes the bellows to expand or contract.

In another embodiment, the present invention provides a self-regulated lung in a manikin further comprising a pressure sensor situated inside the bellows, a syringe pump disposed along the first conduit intermediate the bellows and the mass flow controller, wherein the syringe pump is capable of injecting a volatile drug into the bellows, and a gas analyzer disposed along the second conduit intermediate the bellows and the vane pump, wherein the gas analyzer is capable of assaying the expelled gases.

In addition, another embodiment provides an apparatus for continuously injecting and volatilizing a volatile drug in real time in an integrated patient simulator during simulated medical procedures, comprising a manikin, a supply of gas, at least one output device associated with the manikin, a means for volatilizing a drug administered to the manikin comprised of a thermal conductor defining a gas propagating cavity disposed therethrough and a sintered insert disposed within the gas propagating cavity, the thermal conductor further defining a needle accepting cavity which communicates the exterior of the thermal conductor with the interior of the insert, wherein the needle accepting cavity is capable of accepting a hypodermic needle such that the tip of the hypodermic needle is in contact with the sintered insert when the needle is fully inserted into the volatilizing means, and wherein the gas propagating cavity is capable of permitting the flow of the gas therethrough such that the drug upon evaporation in the sintered insert is carried through the gas propagating cavity by the supply of gas flowing continuously therethrough, a conduit interconnecting the supply of gas with the gas propagating cavity, and programmed computing means associated with the receiving means for calculating a simulated response to the drug and for actuating the output device to simulate the effects of the drug according to a time- and event-based script, a computer model or a combination of a time- and event-based script and a computer model based on the physiological state of the patient simulator. In a preferred embodiment the sintered insert is comprised of brass and the thermal conductor comprises a cylinder of copper.

Another embodiment describes an apparatus for simulating bronchial resistance or dilation in real time in an integrated patient simulator during simulated medical procedures, comprising a manikin with a simulated trachea and a simulated lung, a conduit interconnecting the simulated trachea and the simulated lung for propagating the volume of gas, a volume of gas flowing within the conduit, and a means in the conduit for restricting the flow of the volume of gas therethrough whereby a bronchial opening is simulated. In a preferred embodiment, this conduit is interrupted by an opening and the restricting means comprises rotating means and a nautilus shaped cam mounted on the rotating means so as to present a selected surface thereof within the opening so as to continuously vary the size of the opening.

In addition, the present invention provides an apparatus for detecting and identifying a drug or fluid admired in real time in an integrated patient simulator during simulated medical surgery, comprising a manikin, a bar code affixed to an implement for administering a fluid to the manikin, wherein the implement is selected from the group consisting of an intravenous drip bag and a syringe and wherein the bar code indicates the type and volume of fluid contained within the implement, and a bar code scanning means for detecting and identifying the fluid administered by the bar code affixed to the implement. In a related embodiment, there is provided an apparatus for quantifying the amount of a fluid administered in real time in an Integrated patient simulator during simulated medical surgery, comprising a manikin, a reservoir associated with the manikin for containing a fluid administered to the manikin, a means for delivering the fluid to the reservoir, weighing means for calculating an initial weight of the reservoir and a second weight of the reservoir upon a preselected event, means for calculating the difference between the second weight of the reservoir and the initial weight of the reservoir, and programmed computing means for calculating a simulated response to the quantity of fluid delivered to the reservoir according to a time- and event-based script, a computer model or a combination of a time- and event-based script and a computer model based on the physiological state of the patient simulator.

In a further embodiment, there is provided an apparatus for synchronizing output devices related to a cardiac rhythm in real time in an integrated patient simulator during simulated medical surgery, comprising a manikin, at least one output device associated with the manikin, a first programmed computing means capable of generating at least one electric cardiac rhythm synchronizing pulse, a distributed processing network associated with the manikin, and a second programmed computing means associated with the manikin for calculating a simulated response to the cardiac rhythm synchronizing pulse and for actuating via the distributed processing network the output device associated with the manikin in real time according to a time- and event-based script, a computer model or a combination of a time- and event-based script and a computer model based on the physiological state of the patient simulator. In a preferred embodiment, the distributed processing network is a star network. In a further preferred embodiment, the output device may be a radial pulse emulating means.

The present invention also provides an apparatus for simulating sounds of breathing in real time in an integrated patient simulator during simulated medical procedures, comprising a manikin, a means associated with the manikin for continuously determining the volume of at least one lung bellows associated with the manikin, means for calculating a first derivative of the bellows volume over time to determine the phase of the respiratory cycle and for calculating a second derivative of the bellows volume over time to determine a transition in phase of the respiratory cycle, and sound output means for outputting, based upon the first and second derivatives of the bellows volume over time, an audible sound of breathing corresponding to an appropriate physiological sound. In a preferred embodiment, the sound simulating apparatus has a means for determining whether an abnormal condition is effecting the physiological state of the patient simulator and means for altering the audible sound of breathing corresponding to the appropriate physiological sound based upon the abnormal physiological condition effecting the physiological state.

A similar embodiment encompasses an apparatus for simulating heart sounds in real time in an integrated patient simulator during simulated medical procedures, comprising a manikin, a means for continuously determining the physiological state of the patient simulator, and sound output means for outputting, based upon the physiological state, an audible heart sound corresponding to an appropriate physiological sound. In a preferred embodiment, the heart sounds apparatus further comprises a means for determining whether an abnormal condition is effecting the physiological state of the patient simulator and means for altering the audible heart sound corresponding to the appropriate physiological sound based upon the abnormal condition effecting the physiological state.

Another similar embodiment encompasses an apparatus for simulating lung sounds in real time in an integrated patient simulator during simulated medical procedures, comprising a manikin, a means for continuously determining the physiological state of the patient simulator, and sound output means for outputting, based upon the physiological state, an audible lung sound corresponding to an appropriate physiological sound. Preferably the lung sounds apparatus further comprises a means for determining whether an abnormal condition is effecting the physiological state of the patient simulator and means for altering the audible lung sound corresponding to the appropriate physiological sound based upon the abnormal condition effecting the physiological state.

The integrated patient simulator of the instant invention also provides an apparatus: for simulating the determination of continuous blood gases in real time in an integrated patient simulator during simulated medical procedures, comprising a manikin, a mock continuous blood gas machine associated with the manikin and having a means for simulating an output, means for determining the physiological state of the patient simulator, and a means for delivering a signal to the mock continuous blood gas machine according to the physiological state whereby an output is simulated on the means for simulating an output.

In addition, another embodiment of the integrated patient simulator is an apparatus for simulating a difficult airway in real time in an integrated patient simulator during simulated medical procedures, comprising a manikin having a neck, an airway within the neck which is flexible or crushable along a portion of its length, a programmable computing means for calculating a simulated response to the physiological state of the patient simulator in real time according to a time- and event-based script, a computer model or a combination of a time- and event-based script and a computer model, and based on the calculated simulated response, a means for constricting, sealing or crushing the portion in the airway. In a preferred embodiment, the flexible airway comprises a conduit having a flat back wall having opposed, parallel sides therealong and an exterior surface and an opposed interior surface, a semicircular front wall having edges connected to the respective sides of the flat back wall and having an interior surface and an opposed exterior surface, a plunger disposed adjacent the exterior surface of the flat back wall, a means for actuating the plunger whereby the plunger engages the exterior surface of the flat back all so as to move the interior surface of the flat back wall a selected distance toward the interior surface of the semicircular wall. In a more preferable embodiment, the plunger is complimentarily shaped to the interior surface of the semicircular wall.

In addition to the above apparatuses, there are also provided a variety of method embodiments. First, there is a method of simulating a self-regulated lung in real time in an integrated patient simulator during simulated medical procedures using a manikin, comprising the steps of expanding in volume at least one bellows by a bellows actuating means, directing to the bellows a gas flow delivered by at least one mass flow controller, continuously monitoring the pressure inside the bellows, contracting in volume the bellows by the bellows actuating means continually expelling the gas through a vane pump, and analyzing the expelled gas flow prior to its entry into the vane pump. In a preferred embodiment, the method further comprises the step of continuously injecting via a syringe pump a preselected amount of a volatile drug into the gas flow intermediate the mass flow controller and the bellows. In addition, a preferred embodiment uses a bellows actuating means comprised of a first constant pressure and a second variable pressure acting on respective sides of a double acting piston whereby varying the second variable pressure causes the bellows to simulate, expand or contract depending upon a time- and event-based script, a computer model or a combination of a time- and event-based script and a computer model based on the physiological state of the patient simulator.

In another embodiment, the present invention provides a method of simulating a physiological response to a drug in real time in an integrated patient simulator during simulated medical procedures using a manikin, comprising the steps of directing a volatile drug to a manikin which has a drug volatilizing means, wherein the drug volatilizing means comprises a thermal conductor defining a gas propagating cavity disposed therethrough and a sintered insert disposed within the gas propagating cavity, the thermal conductor further defining a needle accepting cavity which communicates the exterior of the thermal conductor with the interior of the insert, wherein the needle accepting cavity is capable of accepting a hypodermic needle such that the tip of the hypodermic needle is in contact with the sintered insert when the needle is fully inserted into the receiving means, flowing a gas through the gas propagating cavity such that the drug upon evaporation on the sintered insert is carried through the gas propagating cavity by the gas to a drug analyzing means, detecting by the drug analyzing means the kind of drug administered, using that information in computing a simulated response on at least one output device associated with the manikin so as to provide a simulated response in accordance with an appropriate physiological response to the drug.

In yet another embodiment, the present invention provides a method of simulating bronchial resistance or dilation in real time in an integrated patient simulator during simulated medical procedures using a manikin, comprising the step of actuating a means associated with the manikin for restricting a simulated bronchial opening by rotatably engaging a cam that presents a selected surface thereof within an opening in a conduit so as to vary the size of the opening.

A further embodiment provides a method of simulating non-linear compliances in real time in an integrated patient simulator during simulated medical procedures using a manikin, comprising the steps of computing the volume of at least one bellows and supplying a first constant pressure and a second variable pressure acting on respective sides of a double acting piston capable of actuating the bellows whereby varying the second variable pressure causes the bellows to exhibit the desired compliance force on the bellows according to a time- and event-based script, a computer model or a combination of a time- and event-based script and a computer model based on the physiological state of the patient simulator.

Another embodiment of the present invention provides a method of detecting and identifying a drug or fluid administered in real time in an integrated patient simulator during simulated medical surgery using a manikin, comprising the steps of scanning a bar code affixed to an implement selected from the group consisting of an intravenous drip bag and a syringe, wherein the bar code indicates the type and concentration of fluid contained within the implement detecting and identifying the drug administered by the scanned bar code.

Furthermore, there is provided an embodiment of a method of quantifying the amount of a fluid or drug administered in real time in an integrated patient simulator during simulated medical surgery using a manikin, comprising the steps of calculating an initial weight of a reservoir for containing a fluid administering the fluid to the reservoir, detecting a second weight of the reservoir at a preselected event after the administration of the fluid, computing the difference between the second weight of the reservoir and the initial weight of the reservoir, and based on the difference, determining a simulated response to the fluid according to a time- and event-based script, a computer model or a combination of a time- and event-based script and a computer model based on the physiological state of the patient simulator.

In addition, the present invention provides a method of synchronizing cardiac rhythm related events in real time in an integrated simulator during simulated medical procedures using a manikin, comprising the steps of transmitting throughout a distributed processing network associated with the integrated patient simulator at least one electric pulse corresponding to a cardiac rhythm synchronizing pulse and calculating a physical response to the cardiac rhythm synchronizing pulse in at least one output device associated with the manikin. In a preferable embodiment, the distributed processing network is a star network. In an even more preferable embodiment, there is a further step of actuating the at least one output device such as a radial pulse emulating means.

In addition, the present invention provides a method of simulating sounds of breathing in real time in an Integrated patient simulator during simulated medical procedures using a manikin, comprising the steps of continuously determining the volume of at least one bellows associated with the manikin, calculating a first derivative of the bellows volume over time to determine the phase of the respiratory cycle, calculating a second derivative of the bellows volume over time to determine a transition in phase of the respiratory cycle, and directing, based upon the first and second derivatives of the bellows volume over time, through a sound outputting means an audible sound of breathing corresponding to an appropriate physiological sound. In a preferred embodiment, the method further comprises the steps of determining whether an abnormal condition is effecting the physiological state of the patient simulator and altering the audible sound of breathing corresponding to the appropriate physiological sound based upon the abnormal condition effecting the physiological state.

Similarly, another embodiment provides a method of simulating heart sounds in real time in an integrated patient simulator during simulated medical procedures using a manikin, comprising the steps of continuously determining the physiological state of the patient simulator and directing, based upon the physiological state, rough a sound outputting means an audible heart sound corresponding to an appropriate physiological sound. Preferably, this method further comprises the steps of determining whether an abnormal condition is effecting the physiological state and altering the audible heart sound corresponding to the appropriate physiological sound based upon the abnormal condition effecting the physiological state.

In a related embodiment, there is a method of simulating lung sounds in real time in an integrated patient simulator during simulated medical procedures using a manikin, comprising the steps of continuously determining the physiological state of the patient simulator and directing, based upon the physiological state, through a sound outputting means an audible lung sound corresponding to an appropriate physiological sound. In a preferable form, this method further comprises the steps of determining whether an abnormal condition is effecting the physiological state and altering the audible lung sound corresponding to the appropriate physiological sound based upon the abnormal condition effecting the physiological state.

Another embodiment discloses a method of simulating the monitoring of continuous blood gases in real time in an integrated patient simulator during simulated medical procedures using a manikin, comprising the steps of continuously determining the physiological state of the patient simulator, computing appropriate blood gas information based on the physiological state, and delivering a signal to a mock continuous blood gas machine according to the physiological state whereby an output is simulated.

In addition, there is a provided an embodiment which is a method of simulating a difficult airway in real time in an integrated patient simulator during simulated medical procedures using a manikin, comprising the steps of calculating a simulated response to the physiological state of the patient simulator according to a time- and event-based script, a computer model or a combination of a time- and event-based script and a computer model, and based on the appropriate simulated response, constricting a flexible airway in the neck of the manikin.

BRIEF DESCRIPTION OF THE FIGURES OF DRAWINGS

DETAILED DESCRIPTION OF THE ILLUSTRATIVE EMBODIMENTS OF THE INVENTION

Figure 1:
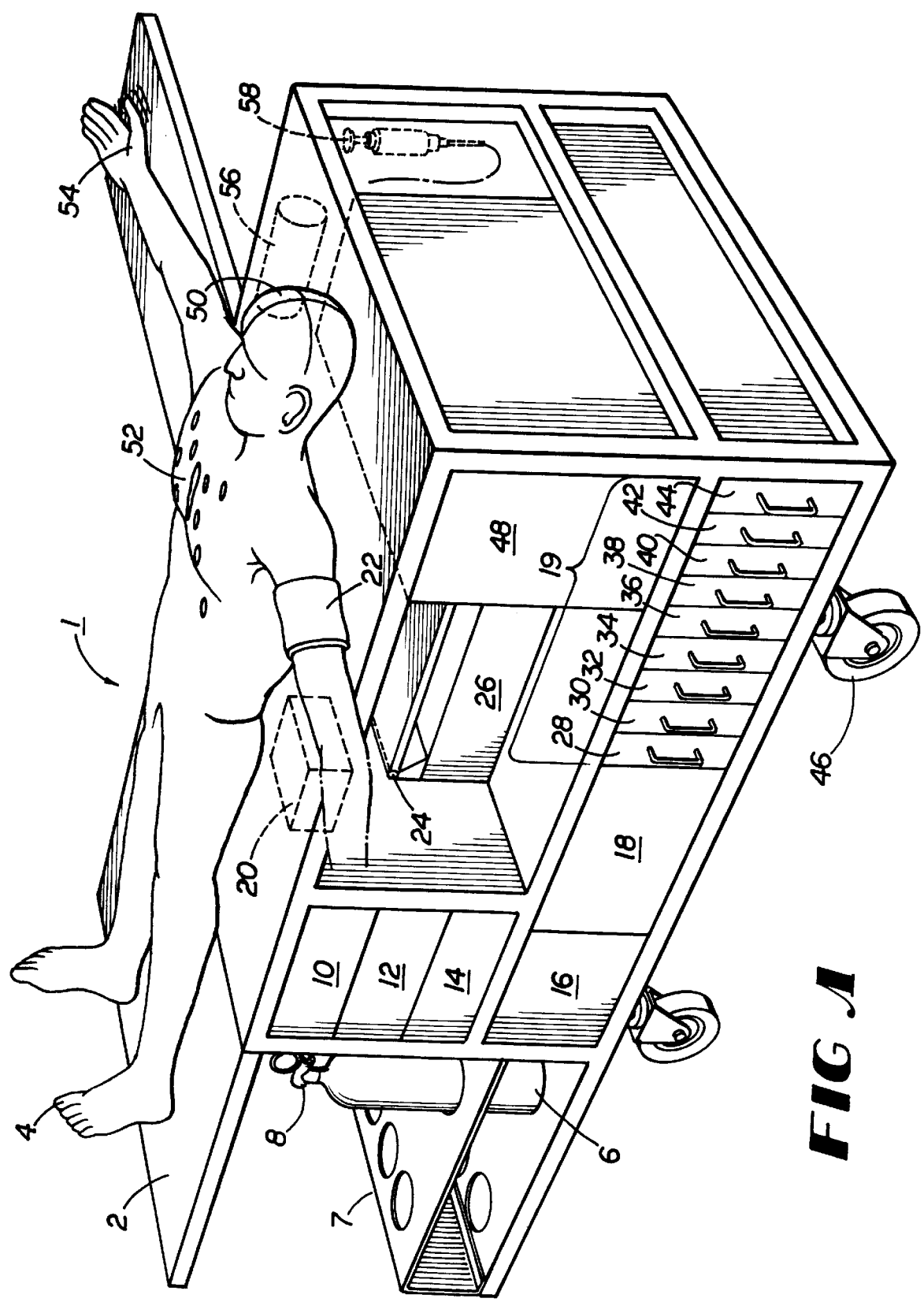
FIG. 1 is a perspective full view of the present integrated patient simulator with the subsystems included therein indicated.

One embodiment of the current invention comprises a computer-based physiologic model covering the following subsystems: cardiovascular; uptake and distribution; neuromuscular; pharmacokinetics/pharmacodynamics and physiologic control models. Also included is a unique way of linking the different subsystems to realistically simulate the interactions between the subsystems and the control system in response to the actions of a trainee, student, or other user (including input from both a computer peripheral such as a mouse/keyboard, wired remote keypad, wireless remote control unit, barcode reader and from sensors physically embedded in the full scale lung/patient simulator).

A significant part of a patient simulator useful for training anesthesiologists and other physicians comprises a subsystem to perform gas exchange. The lung model on the instant integrated patient simulator consumes and produces gases, just like a human lung. Uptake and excretion of $O_2$, $CO_2$, $N_2$, $N_2O$ and volatile anesthetic gases are physically created and simulated, based on the measured concentrations in the bellows of the simulated lung and in a software model representing uptake, distribution, storage, consumption, and/or production in the body. Lung perfusion is also accounted for in this model by modeling of the cardiovascular subsystem of the patient being simulated by the physiological model. Alveolar ventilation is dependent on the lung mechanics and, in the case of spontaneous breathing, is driven by the physiologic control and pharmacokinetics/pharmacodynamics models. See Guyton, A. C., *Textbook of Medical Physiology* (8th ed.), W. B. Saunders Co., Philadelphia, 1991.

The lung model portion of the patient simulator is capable of simulating spontaneous breathing with computer control of tidal volume (VT) and respiratory rate (RR). Spontaneous movement of the bellows is driven by an analog muscle pressure signal to simulate inspiration, active expiration, coughing, and different spontaneous breathing patterns (I/E [inhalation/exhalation] ratio, respiratory rate, respiratory patterns associated with light anesthesia. The respiratory rate is the frequency of the muscle pressure signal while tidal volume depends on the amplitude of the muscle pressure signal as well as other airway parameters such as bronchial resistances and lung-thorax compliances). The muscle pressure signal is generated by the physiologic control model based on arterial blood $O_2$ and $CO_2$ content. The signal is converted by a digital to analog converter into a physical signal directed to the electronic pressure regulators (EPRs). The real and time-variable voltage thus obtained is fed to the subsystems of the patient simulator including the electronic pressure regulator (EPR). The $O_2$ and $CO_2$ contents are variables of an uptake and distribution model, with the gas concentrations in the bellows as an additional input. Under normal operating conditions (i.e., non-occluded airway and normal gas circulation), normal arterial $O_2$ and $CO_2$ contents are maintained. Depression of spontaneous breathing by the influence of anesthetic drugs on the respiratory center and/or by the effect of muscle relaxants directly on the respiratory muscles is provided by the pharmacokinetic/pharmacodynamic software models. In addition, normal and abnormal breath sounds are synchronized with the bellows movement.

Furthermore, variable resistances under software control can be varied during the respiratory cycle to simulate partial collapse of the airways during expiration. This variability includes non-linear computer controlled compliances (i.e., the inverse of the stiffness of the lung) and computer controlled functional residual capacity (FRC). Existing simulators with lung modeled are capable of linear compliance only. This is unrealistic in that the human lung exhibits a compliance (volume versus pressure) curve which is sigmoidal in nature.

Non-linear compliances allow the simulation of variable stiffness of the lung. This is accomplished via double acting pneumatic pistons as described herein. Then, passive forces resulting from the non-linear lung- thorax- diaphragm compliances are computed, taking into account lung volume and intrapleural volume. An intrathoracic pressure is generated, affecting circulation and, thereby, gas exchange. The resulting forces on the lung bellows are realized through a double acting piston disclosed more fully herein. Compliances and target or modeled intrapleural volumes are under software control.

Thus, with the above-described stimuli, the patient simulator is able to generate various clinical signs including a sound storage and triggering mechanism and localization of sound sources/speakers. In particular, speakers have been localized to simulate both heart and lung sounds in locations generally known to those skilled in the art. See, generally, FIG. 1. Finally, the patient simulator can generate an electrocardiogram (ECG) spike synchronization pulse which is distributed over the network for use by all cardiovascular related signals, variables or parameters.

Furthermore, the simulation of blood gas values to corroborate/support scenarios being played has been implemented. Also disclosed is the simulation of of detection of pulmonary artery (PA) catheter balloon inflation and associated changes in the PA pressure.

The gas substitution technique together with the physiological software models create a self-regulating lung that changes its own breathing pattern. Specifically, the patient simulator can change its inspiratory muscle pressure waveform to maintain a preset level of arterial/alveolar $pCO_2$ and $pO_2$ (partial pressures). The double acting piston mechanism (including a shaft encoder) and its self-regulating software model create spontaneous breaths of variable size and shape along with independently variable compliance and independently variable bronchial resistance. Thus, the patient simulator disclosed herein contains a hybrid (mechanical and mathematical) lung model which regulates itself regardless of what type of gas (air, anesthetics, hypoxic, etc.) is inhaled. In addition, even the blunting of physiological control mechanisms (e.g., ventilatory response to carbon dioxide) is self-regulated.

Therefore, the patient simulator provides a robust system which reacts upon user interaction with the lung model (for example, if the user changes the inspired gas composition). Thus, when a user changes the inspired gas composition, this change causes changes to the physically simulated alveolar concentrations of the various gases. The physiological model win then determine the effects of these changes in gas concentrations in the lung and, in fact, upon the entire physiological state of the integrated patient simulator. The lung model physically simulates these changes (for example, by decreasing spontaneous breathing). Furthermore, the lung model changes result in a different composition of gas being exhaled and thereby realistically measured by the external monitoring instruments. Finally, the user may react to these changes by further changing the inspired gas composition, and thus initiating a cyclical repeat of the interactive steps described above.

Referring now to FIG. 1, it is helpful to gain a general understanding of the spatial orientation of the various subsystems of the preferred embodiment of the present patient simulator. The patient simulator 1 consists of a manikin 4 placed atop a table 2. The table 2 itself is of the same physical dimensions as tables used in operating rooms and hospitals. Interposed in various positions below the table are the control and implementation devices associated with several of the subsystems of the integrated patient simulator.

Manikin 4 is constructed of plastic and has a means 54 for effecting a thumb twitch as described in U.S. application Ser. No. 07/882,467. In addition, area 52 of this manikin indicates the general area for placement of heart and lung sound devices subcutaneous to the manikin 4. A head 50 (Laerdal Medical Corp., Armonk, N.Y.) is provided attached to the manikin 4. Head 50 contains the mechanism for simulation of difficult airway 700 (FIG. 8) and means for permitting cricothyrotomy (not shown). Attached to one arm of manikin 4 is a non-invasive blood pressure monitor (NIBPM) 22. Signals from the NIBPM 22 are directed to card 36 described infra.

Interposed beneath table 2 are various devices which will now be described in more detail. Gas cylinders 6 are situated near the foot end of the manikin 4 in an array of gas cylinder holders 7. Attached to the gas cylinders 6 are regulators 8 for regulating the flow of gases. Cylinders 6 for $O_2$, $CO_2$, $N_2$ and $N_2O$ are provided. However, cylinders of other gases may be added depending on need.

Just forward of the gas cylinders 6 are interposed various instruments 10, 12 and 14. A pulse oximeter stimulator 10 is provided to stimulate the pulse oximeter. Just below the oximeter stimulator 10 is placed an IV drug collection vessel with a digital scale 412 (Denver Instrument Co., Arvada, Colo.) (See FIG. 5). Below the drug collection and quantification device, collectively labeled 12, is placed a NIBPM stimulator 14. The NIBPM stimulator 14 interfaces with NIBPM 22 and module 36 which in turn interfaces with the computer 16. Computer 16 is situated under the NIBPM stimulator 14 and next to a power supply 18 capable of powering the complete patient simulator 1.

Figure 7:
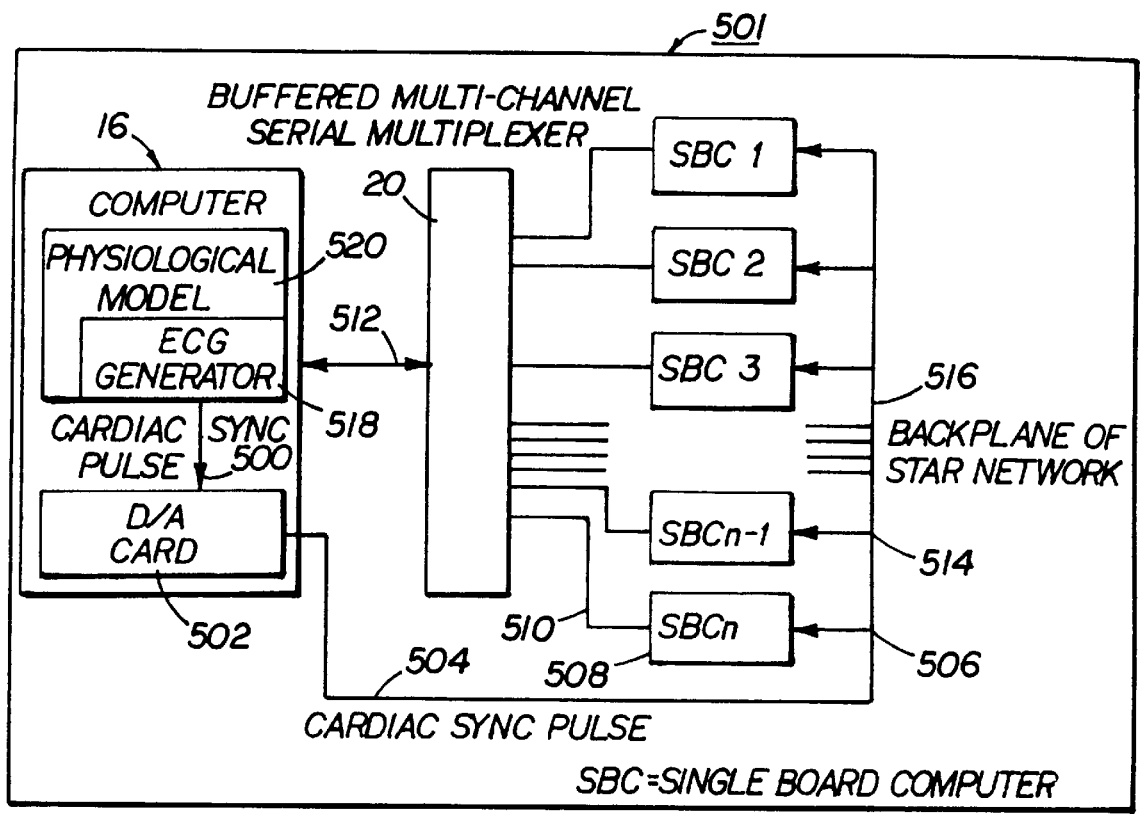
FIG. 7 is a schematic of a star configuration distributed processing network and a schematic of the path for an electric cardiac synchronization pulse throughout the star configuration distributed processing network.

Situated behind instruments 10, 12 and 14 is a multiplexer 20 responsible for the routing and handling of data signals for Inputs and outputs as utilized in the preferred star network configuration 501 (See FIG. 7). Adjacent to multiplexer 20 and power supply 18, is interposed a rack 19 of plug in modules 28, 30, 32, 34, 36, 38, 40, 42 and 44. In the preferred embodiment, module 28 is responsible for the generation of heart sounds. Module 30 is responsible for the generation of the ECG. Module 32 is responsible for generating lung and breath sounds. Module 34 is responsible for portions of the lung simulator: the gas exchange and mass flow controllers 122. Module 36 is responsible for the palpable pulses (not shown), NIBPM 22 and bronchial resistances (See FIG. 4). Module 38 is responsible for the drug identification and quantification subsystems. Module 40 is included for simulating machine and/or equipment failures of an anesthesia machine. Module 42 drives the thumb twitch mechanism 54. Finally, module 44 drives other portions of the lung simulator: the lung mechanics 26 and the two EPRs 108 (See FIG. 2). Those skilled in the art would realize that other desirable modules could be included in an expanded rack 19 and that the order of modules is unimportant.

The lung assembly 26 (Michigan Instruments, Inc., Grand Rapids, Mich., Dual-Adult Test Lung) is interposed below table 2 and manikin 4. Also shown is a pivot 24 point which is part of the bellows mechanism (See FIG. 2). Forward of the lung assembly is a gas analyzer 48 (Hewlett Packard M1025A, Palo Alto, Calif.) into which is fed the gases from the bellows 100 of the lung 26. Opposite gas analyzer 48 is situated a syringe pump 58 and associated copper block mechanism 56 (See FIG. 3).

The various subsystems are connected as follows. Signals from computer 16 are routed through multiplexer 20 and to the rack 19 of modules. Appropriate inputs are determined from sensors placed throughout the manikin 4, e.g., intravenous drug administration detection means. In addition, various outputs are routed through the multiplexer 20 and via the modules 28, 30, 32, 34, 36, 38, 40, 42 and 44 to appropriate output devices, including speakers for heart and lung sounds near 52, difficult airway simulation (See FIG. 8) 700 in the trachea area of head 50 (See FIG. 4), thumb twitch 54, movement of lung mechanism 26, etc.

By "physiological model," it is intended that the computer 16 may regulate the behavior and interaction of the various subsystems so that they behave in a manner consistent with a human patient. Thus, depending upon the parameters, e.g., sex, age, body mass cardiac output, shunt fraction, etc., the current invention allows the simulation of healthy and diseased (e.g., emphysema) patients of various ages and both genders. Other models may be rendered limited only by the scope of modeling desired. A particular desired physiological model could be rendered by one skilled in the art with knowledge of the mathematical behavior of the systems to be simulated.

By "physiological state," it is meant the totality of all physically relevant data, e.g., blood pressure, heart rate and cardiac outputs. The physiological state includes simulated temperature, gas content in the lungs, anesthetic drug involved including quantity and other information. In addition, compliance of the lung, whether the patient is exhaling or inhaling, has a difficult airway or bronchial resistance are all factors which in their totality will dictate the physiological state of the patient simulator 1. The list just described is expressly meant to be non-limiting, and the particular physiological information tracked will depend upon the particular embodiment desired and the relevant physiological model. The information about the physiological state constitutes the data used by computer 16 in implementing a particular physiological model.

By "programmed computing means," it is meant the combination of the computer 16 which controls the single board computers, e.g., 508, which manage the various subsystems of the current patient simulator 1. The programmed computing means thus exists atop a distributed processing network 501 as described elsewhere herein and known to those skilled in the art. The necessity to convert digital inputs and outputs to analog puts and outputs is modeled as appropriate but such devices are generally not shown in the schematic figures. However, one skilled in the art would readily be able to determine their necessity and implementation, as well as the overall wiring scheme needed by examining U.S. patent application Ser. No. 07/882,467 and the information contained herein.

Thus, time and event based scripts are run based on the computer 16 intervention or instructor intervention with the system. The events may be scripted or non-scripted as appropriate for the desired simulated application. A combination of time- and event-based scripts is possible where needed. For instance, an instructor may determine that a difficult airway situation should arise by using an event-based script. In response, the physiological model is used to model the behavior of the simulator in response to the scripted difficult airway event which is physically created. The scripts readily interface with the physiological state information as well as the physiological model.

The specific embodiments of the patient-simulator and methods of using it are disclosed more fully in the following non-limiting examples of the best mode of carrying out the invention.

EXAMPLE I

Self-regulating Mechanical Lung

During simulated spontaneous breathing, the breathing software model determines a respiratory muscle activity based on arterial carbon dioxide and oxygen partial pressures. This respiratory muscle activity drives the mechanical lung model in the instant patient simulator by generating breaths of variable amplitude and frequency. The partial pressures of the gases inside the mechanical lung model (i.e., "alveolar" partial pressures) depend on this breathing pattern, on the composition of the inspired gas and on the uptake or delivery of the gases to the alveolar space. The uptake or delivery is computed by a software physiological model and physically generated by a gas substitution technique. The alveolar partial pressures (part of the physiological state) are inputs to an uptake and distribution software model portion of the physiological model that computes the arterial carbon diode and oxygen partial pressures.

During the simulation of normal conditions, the resulting alveolar ventilation is sufficient to eliminate the carbon dioxide produced and to supply oxygen for consumption. Thus, in normal conditions, physiologically correct carbon dioxide and oxygen partial pressures result and the alveolar partial pressures can be approximated at the end of expiration by unaltered airway gas analyzers or monitors. The arterial partial pressures are visualized on a modified continuous blood gas analyzer (Puritan Bennett PB 3300, Lenexa, Kans.) (i.e. supplying the correct pressure, concentration, voltage, current, etc. signals) it through serial RS-232 links.

Under abnormal conditions, the self-regulating mechanical lung reacts in a realistic way to simulated conditions. Some conditions which may thus be simulated include the administration of inspiratory gas containing too little oxygen or too much carbon dioxide, assisted ventilation causing hyperventilation, (partial or complete) airway occlusion and instructor controlled, simulation generated, or physiological model dictated modification of programmable lung and thorax compliances. In addition, depression of simulated circulation in the cardiovascular software model and simulation of drug treatment affecting spontaneous breathing and/or circulation may also be accomplished by the current patient simulator.

A. Implementation of the lung mechanics

Figure 2:
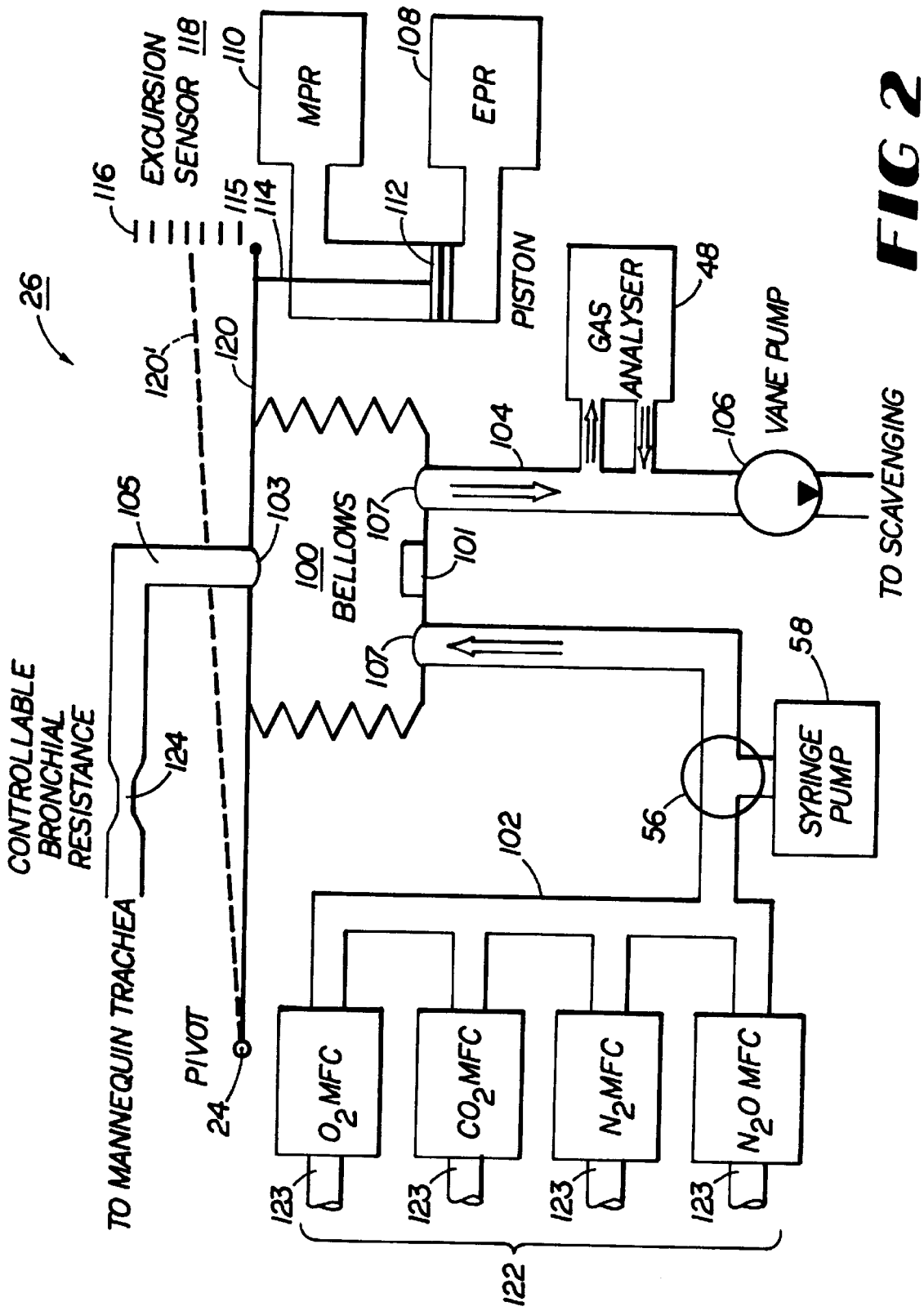
FIG. 2 is a schematic view of the lung of the integrated patient simulator of the present invention.

Referring to FIG. 2, the lung volumes are realized by mechanical bellows 100. The volume of the bellows is derived from an excursion sensor 118. The excursion sensor 118 consist of a rack 116 and pinion (not shown) arrangement. One end of the rack 116 is attached to the top plate 120 of the bellows 100. The other end of the rack 116 is free. The pinion is engaged into the rack 116 and has a shaft encoder (not shown) mechanically coupled to it. As the lung bellows 100 volume changes, the rack 116 moves with the top plate 100 and rotates the pinion and thus the shaft encoder. Thus, after initialization, the volume of each lung bellows 100 is known at all times. Note that there is one excursion sensor 118 for each of the two bellows 100 allowing independent volume measurement for simulated left and right lungs. The piston rod (a shaft attached to a pinion) 114 of the double acting piston 112 is attached to the bottom of plate 120. As the lung bellows 100 volume changes, e.g., as the plate 120 moves from its rest position to position 120', the rack 116 moves with the top plate 120 and thus the pinion turns the shaft encoder 115. Thus, after initialization, the volume of each lung bellows 100 is known at all times. There is a separate excursion sensor 118 for each of the two bellows 100 used in the preferred embodiment.

The software on the personal computer 16 that drives the lung 26 uses an analog respiratory muscle pressure signal generated by the software control model of spontaneous breathing. In addition, the software model uses the left and right lung excursions 118 as inputs. Based on these inputs, the model computes the pressures exerted by programmed non-linear lung and thorax compliances. Left and right intrapleural pressures follow from these computations. Computer-controlled electronic pressure regulators (EPRs) (Proportion-Air, McCordsville, Ind., model # QBITFEE050) 108 are fed with an inspiratory pressure signal (where frequency of the signal is the breathing frequency and magnitude is the tidal volume) causing them to then drive a double acting pneumatic piston 112 (Clippard, Cincinnati, Ohio) (one for each lung). In addition to the EPR 108, there is a manual pressure regulator (MPR) 110 responsible for imparting a constant (i.e., a bias or reference) pressure on the double acting piston 112. The MPR 110 of the present invention produces about 25 psig of constant bias pressure. However, those skilled in the art would appreciate that other, mechanically feasible bias pressures are contemplated.

The force created by the piston 112 is equivalent to the force resulting from the intrapleural pressure, and the lung compliance on the natural lung. Based upon the above interactions, the bellows 100 realistically simulates the pressure-volume (and thereby the pressure-flow) characteristics of the natural lung.

Various physiologic parameters under computer 16 control may be set and modified in educational scenarios, include bronchial resistances 124, lung and thorax compliances, and intrapleural volume allowing for the simulation of respiratory complications such as endobronchial intubation, bronchospasm, pneumothorax, and emphysema according to an appropriate physiological model.

B. Implementation of the gas exchange

Uptake and delivery of the alveolar gases inside the bellows 100 are physically created by gas substitution. The gases presently contemplated are $O_2$, $CO_2$, $N_2$, $N_2O$, and one volatile anesthetic agent (i.e., isoflurane, enflurane, or halothane) (M. L. Good, S. Lampotang, G. Ritchie, et al: Hybrid lung model for use in anesthesia research and education, *Anesthesiology* 71, p. 982, 1989). In gas substitution, a constant gas flow rate with a variable composition, thereby constantly flushing the bellows 100, simulates the pulmonary blood flow, carrying gases to and from the lungs. The vane pump 106 (GAST 0532, Benton Harbor, Mich.) of FIG. 2 realizes the constant, volumetric flow rate (and, because it is a rotational device, eliminates the vibration associated with a reciprocating device), and the computer 16 driven mass flow controllers 122 (Omega Engineering, Stamford, Conn.) allow for adjustment of the inflow composition. Uptake and delivery are computed based on the measured alveolar partial pressures (from the gas analyzer 48) and venous partial pressures from the uptake and distribution software model, taking into account perfusion and solubility.

Thus, gas is fed to the mass flow controllers 122 through feed lines 123 originating in gas cylinders 6 and regulators 8. In addition, computer 16 signals the MFCs 122 to provide a set flow rate of the appropriate gas into tubing or conduit 102 which is resistant to volatile anesthetics. In the preferred embodiment, silicon tubing with a ⅛" diameter is used for conduit 102. The gas contained in the conduit 102 is passed rough a copper block 56 as described in FIG. 3. Input of any liquid anesthetic occur in the syringe pump assembly 58 (Harvard Apparatus, Inc., Pump 22, South Natick, Mass.) and the volatilized gas b moved toward bellows 100 due to the flow of gases present in the conduit 102. In this way, gases are introduced via the conduit 102 Into the bellows 100. Once in the bellows 100, gas pressure may be constantly assayed using pressure sensors 101. In addition, down force of the bellows by movement of plate 120 on pivot 24 results in expulsion of gas from the bellows 100 trough conduit 105. Conduit 104 leads to a gas analyzer 48 where the gas continuously flowing from the bellows can be assayed for its constituents and their concentrations. In addition, conduit 104 leads to vane pump 106 which rotatably allows a constant flow rate of gas to escape to a scavenging area (not shown).

In addition, bellows 100 contains an aperture 103 leading to an additional conduit 105. Conduit 105 is used by the simulated lung 26 to allow air to flow from the manikin 4 head to the lung 26. Along conduit 105 there is a controllable bronchial resistance means 124 as described herein with reference to FIG. 4. Conduit 105 continues on to the trachea (including difficult airway apparatus 700, shown in FIG. 8) and mouth of the manikin 4.

It should be noted that in the present embodiment, there are actually two sets of bellows 100 and thus two double acting piston mechanisms 112, one attached to each bellows 100 (although only one of each element is depicted in FIG. 2). Thus, there are also two sets of MPR 110 and EPR 108 included. In addition, each bellows 100 contains its own pressure sensor 101. However, most of the conduits 104 and 102 as well as the syringe pump 58, vane pump 106, gas analyzer 48 and MFCs 122 are shared between the simulated "right" and "left" lungs.

Thus, the present invention contemplates a method of simulating a self-regulated lung 26 in real time. The method includes step of expanding in volume at least one bellows 100 by a bellows actuating means, e.g., a double acting piston 112, during an inspiratory phase. A gas flow from at least one mass flow controller 122 is allowed to flow trough a conduit 102 to the bellows 100. The pressure inside the bellows 100 is under continuous monitoring based on the output from a pressure sensor 101. This pressure output is used as one of the inputs to the physiological model coordinated by the computer 16. After the inspiratory phase is completed, an expiratory phase is created by contracting in volume the bellows 100 by the piston 112 acting on plate 120 as previously described. Before expulsion through the vane pump 106, gases transferred to the conduit 104 are analyzed in a gas analyzer 48 which is situated intermediate the vane pump and the bellows in a preferred embodiment.

Furthermore, in a more preferable embodiment, a syringe pump 58 may be situated intermediate the mass flow controllers 122 and the bellows 100. The syringe pump 58 is responsible for continuously (as dictated by the computer 16) injecting a preselected flow rate of a volatile drug into the gas flowing through conduit 102. The actual delivery of the liquid drug to the gas flow is accomplished via the apparatus for receiving a volatile drug 56 described more fully below.

Furthermore, in a preferred embodiment, the bellows actuating means comprises a first constant pressure from an MPR 110 and a second variable pressure from an EPR 108 acting on respective sides of a double acting piston 112 whereby varying the second variable pressure causes the bellows 100 to simulate an expiratory or inspiratory phase depending upon a time- and event-based script, a computer model or a combination of a time- and event-based script and a computer model based on the physiological state of the patient simulator. For instance, the physiological state may indicate that a cough is appropriate. If so, a signal is directed to the EPR 108 by the computer 16 indicating that a rapid decrease in pressure is needed to simulate a cough. Thus, the EPR 108 in responding to the signal will lower or raise the pressure against one side of the double acting piston 112. This will create a pressure imbalance, the degree of which will determine the force and rapidity of movement of the piston 112. The double acting piston 112 by way of its linkage through piston rod 114 and plate 120 will thus forcibly move the top plate 120 of the bellows 100. Movement of the top plate 120 in an upward direction increases the volume of the bellows 100. This increased volume creates a slight subambient pressure in the bellows 100, thereby mimicking inhalation or inspiration. Note that the opposite motion of the piston 112 via piston rod 114 would cause a concomitant expiration or exhalation thereby expelling any gases in the bellows 100 due to the creation of a slight positive pressure.

Thus, in a preferable embodiment, there is provided a self-regulated lung in a manikin 4 for use in real time in an integrated patient simulator during simulated medical procedures, comprising several components. The lung 26 uses at leant one bellows 100 capable of receiving and expelling a gas. Furthermore, there is a means for actuating the bellows between an expanded and a contracted state depending upon a time- and event-based script, a computer model or a combination of a time- and event-based script and a computer model based on the physiological state of the patient simulator. Also present is at least one mass flow controller 122 capable of directing the gas into the bellows 100. To transmit the gas flow there is a first conduit 102 interconnecting the mass flow controller 122 and the bellows 100. In addition, a vane pump 106 capable of expelling the gas from the bellows 100 is provided along a second conduit 104 interconnecting the bellows 100 and the vane pump 106.

In a preferred embodiment, the means for actuating the bellows 100 between an expanded and a contracted state comprises a double acting piston 112 attached to the bellows 100 at its top plate 120 via a rack 116 and piston rod 114 is provided. A first constant pressure from an MPR 110 and a second variable pressure from an EPR 108 act on respective sides of the double acting piston 112 such that varying the second variable pressure causes the bellows 100 to simulate or undergo an expiratory or inspiratory phase. Furthermore, the pinion has a shaft encoder 115 affixed thereto. This encoder 115 is a portion of the excursion sensor 118, which is responsible for reading either the right or the left lung volume of the bellows 100. This value is then used by the computer 16 to simulate a response based upon the excursion value and other data corresponding to the physiological state of the patient simulator 1.

Another preferred embodiment comprises the use of intrapleural pressure sensors 101 situated inside the bellows 100. These devices determine the pressure of the bellows which data form a part of the physiological state of the patient simulator 1. Thus, the computer 16 may take into account the intrapleural pressure so communicated in computing a simulated response of the system, e.g., determining compliance behavior for a particular physiological model based upon the instantaneous lung volume reading.

Another embodiment of the lung 26 allows for placement of a commercially available syringe pump 58 disposed along the first conduit 102 intermediate the bellows 100 and the mass flow controller(s) 122, wherein the syringe pump 58 is capable of injecting a volatile drug into the bellows 100. It should be noted that the conduits 102, 104, and 105 used herein, as well as the other materials in contact with the gas flow, must be resistant to breakdown upon exposure to the volatile drugs used by clinicians. For this reason, silicon tubing is used for the conduits 102, 104, and 105 in the instant embodiment. However, other suitable materials exist and would be known to one skilled in the art.

Finally, a gas analyzer 48 may be disposed along the second conduit 104 intermediate the bellows 100 and the vane pump 106, wherein the gas analyzer 48 is capable of assaying the expelled gases. The information on expelled gases is then transmitted via an electric signal (not shown) to the computer 16. In the computer, based upon the current physiological model and physiological state, a simulated response to the gas analysis is computed. For instance, if no carbon dioxide is being expelled by the modeled lung 26, then an abnormal condition may be deduced in the physiological state.

EXAMPLE II

Injection of Liquid Anesthetic Under Computer Control

Figure 3:
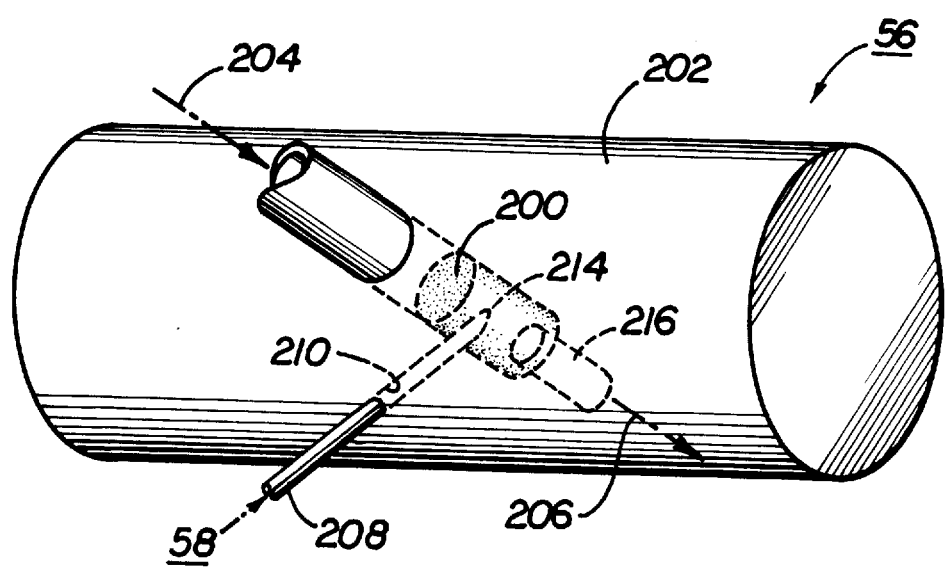
FIG. 3 is a cut-away perspective view of a means for accepting and vaporizing a liquid anesthetic.

Referring now to FIG. 3, the means for accepting the drug 56 comprises a cylindrical copper block 202 with a hypodermic needle having a very small internal diameter (less than 0.01") accepting orifice 210 and a syringe pump 58 (not shown) for injection of liquid anesthetic. Thus, a sintered brass (or other metal) insert 200 is placed in intimate thermal contact within the solid copper cylinder 202 (6" long×2.5" diameter). The tip 214 of a hypodermic needle 208 is passed through a hole 210 (of sufficient diameter to accept a commonly available syringe needle) drilled in the sintered metal insert 200 and secured via a manual push fit. The other end of the hypodermic needle 208 is attached to the tip of a syringe (not shown) loaded with liquid anesthetic and mounted on a computer-controlled syringe pump 58. The syringe is always placed at a lower elevation than the point of injection so that the liquid anesthetic cannot unintentionally flow by gravity into the breathing circuit.

In this configuration, the copper block 202 provides the thermal inertia or heat capacity to prevent freezing at the point of anesthetic injection 214. The sintered insert 200 provides low flow resistance to the passage of gas through the copper block 202, while allowing the liquid anesthetic to wick through it and thus be completely vaporized. The metallic nature of the sintered metal insert 200 provides intimate thermal contact and conduction as compared to, for example, a cotton wad as the injection point. (Ross, J. A. S., Wloch R. T., White D. C. & Hawes D. W.: *Servocontrolled closed circuit anaesthesia: A method for the automatic control of anaesthesia produced by a volatile agent in oxygen,* British Journal of Anesthesia, 55:1053, 1983.) The flow resistance of the very small bore hypodermic needle 208 creates a back pressure of up to 15 psig at the syringe preventing the liquid anesthetic from spontaneously vaporizing at room temperature. Also, the rate of injection of the liquid anesthetic and, therefore, the rate of introduction of inhalational anesthetic into the circuit is independent of the gas flow. The syringe pump 58 is controlled by computer 16 allowing for ease of interfacing.

Thus, the instant invention contemplates a method of simulating a physiological response to a drug in real time in an integrated patient simulator during simulated medical procedures using a manikin. The steps of this method include directing a volatile drug to a manikin 4 which has a drug receiving or volatilizing means 56 comprised of a thermal conductor 202 defining a gas propagating cavity 216 disposed therethrough and a sintered it 200 disposed within the gas propagating cavity 216, the thermal conductor 200 further defining a needle accepting cavity 210 which communicates the exterior of the thermal conductor 202 with the interior of the insert 200, wherein the needle accepting cavity 210 is capable of accepting a hypodermic needle 208 such that the tip 214 of the hypodermic needle 208 is in contact with the sintered insert 200 when the needle 208 is fully inserted into the receiving means 56, and wherein the gas propagating cavity 216 is capable of permitting the flow of the gas 204 therethrough such that the drug upon evaporation or volatilization in the sintered insert 200 is carried through the gas propagating cavity 216 by the supply of gas flowing continuously therethrough and exiting opposite at 206.

Thus, a preferable embodiment comprises an apparatus for injecting and vaporizing a volatile drug in real time in a lung simulator during simulated medical procedures, comprising a manikin 4 and the system described supra. However, there is also a conduit (not designated) for interconnecting the supply of gas 204 with the gas propagating cavity 216.

In a preferred embodiment, the sintered insert 200 is comprised of sintered brass and the thermal conductor 202 is made from a cylindrical piece of copper with the gas propagating cavity 216 bored therethrough.

Thus, the design of this example has application beyond the t patient simulator. Practicing physicians, nurses and anesthesiologists would benefit from the disclosed apparatus with only minor variations to the concepts disclosed above. The combination of a syringe pump injecting liquid anesthetic through a very high flow resistance hypodermic needle in to a sintered metal insert in a cylinder having high thermal capacity can be used as a computer controlled vaporizer in an anesthesia machine or anesthesia delivery system.

EXAMPLE III

Simulation of Bronchial Resistances

Figure 4:
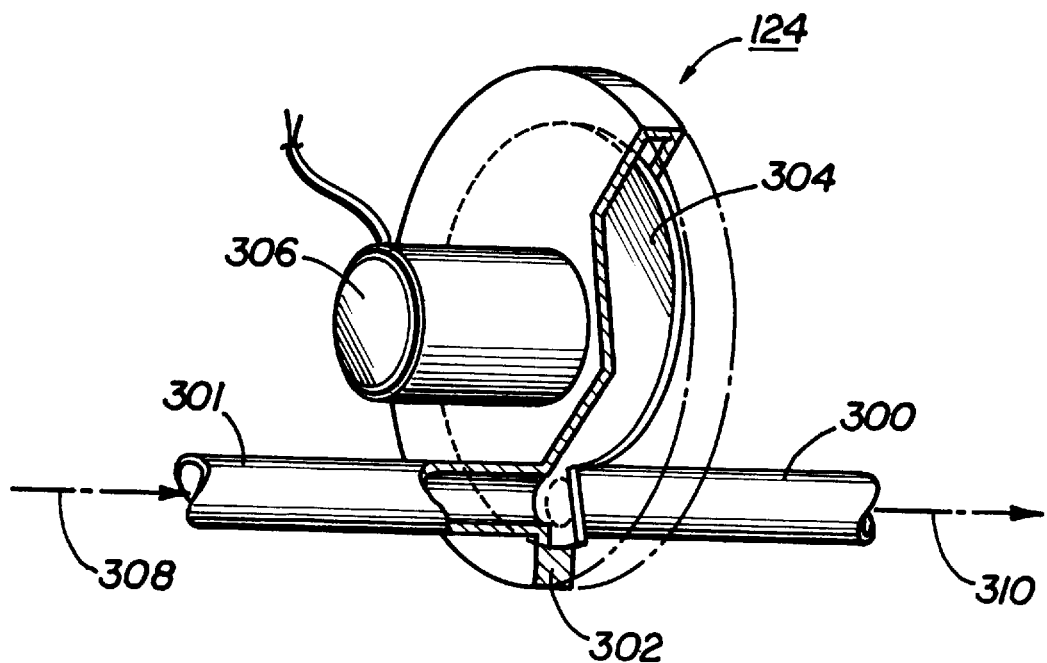
FIG. 4 is a cut-away perspective view of a computer-controlled, motorized variable flow orifice for insertion in the bronchus with a portion of the orifice cut-away for clarity.

Referring now to FIG. 4, a variable orifice device 124 disclosed herein consists of a nautilus shaped cam 304 which is able to progressively block a lumen or conduit 300 or other delivery tube or pipe upon rotation of the cam 304 by a stepper motor 306. Motor control is accomplish ed via module 36 sending a sign to the stepper motor 306. In a preferred embodiment, the cam 304 is within housing 302 and is constructed of thin flexible material (e.g., transparency film) used to vary the flow area through an off-center flow passage 301. The patient simulator 1 may have multiple bronchial resistance devices 124.

Gas 308 flows into the conduit 300 via the conduit's inner passage 301. Depending on the rotational position of the cam 304, the cam 304 presents a selected surface within the passage 301 trough an opening in the conduit 300 so as to partially or totally restrict gas flowing therethrough along the direction 308 and out 310.

Specifically, the present invention discloses a method of simulating bronchial resistance or dilation in real time in an integrated patient simulator during simulated medical procedures using a manikin, comprising the step of actuating a means 124 associated with the manikin 4 for restricting a simulated bronchial opening (as embodied by the inner passage 301 of a conduit 300, by rotatably (via a stepper motor 306) engaging a nautilus shaped cam 304 which, upon rotation, continuously varies the size of the aperture of the simulated bronchial opening.

To accomplish this task, an apparatus (a variable orifice 124) for simulating bronchial resistance or dilation in real time in an integrated patient simulator during simulated medical procedures is disclosed. In addition to the manikin 4 having a simulated trachea (not shown) and a simulated lung 26, the apparatus uses a volume of gas in the direction 308 which enters a conduit 300 for propagating the gas. The gas 308 is used to simulate the flow of gases coming from the trachea during inhalation. In addition, the bronchial resistance means allows for the gas to travel in the opposite direction, from the lung 26 to the trachea as in expiration. The conduit 300 interconnects the simulated trachea and the simulated lung 26 and is interrupted by a means 304 in the conduit 300 for restricting the flow of gas (in either direction) therethrough whereby a bronchial opening is simulated and resulting in a restriction on the gas 308 flowing through the conduit 300. In addition, any catheter or other device inserted into the simulated bronchial opening will be impeded by the presence of a bronchial resistance 124 means.

Such a device 124 provides the following advantages. First, changes in flow resistance can be physically realized in real time. Both the steady state changes and the cyclical changes in airway resistance (variation between inspiratory and expiratory airway resistances during a breath) can be simulated. Each variable orifice 124 in each bronchus can be independently controlled allowing the simulation of lungs with regional differences in time constants. Because the flow of the gases to and from the lung will be physically impeded, the symptoms associated with increased airway resistance will be automatically created. For example, thee capnogram will be appropriately distorted (sloping, instead of flat, plateau) and the dynamic compliance will decrease with increased airway resistance.

The pharmacologic effects of drugs like bronchodilators can be simulated with the variable orifice resistances 124, under control from a pharmacologic model running on the control computer. Furthermore, a suction catheter or other probe can be passed down the bronchus when the flow orifice 124 is not closed. The instant device is capable of producing a multitude of flow-resistance curves. At least 10 different flow resistance curves have been obtained.

EXAMPLE IV

Detection and Identification of Intravenous Drug and Fluid Administration

Figure 5:
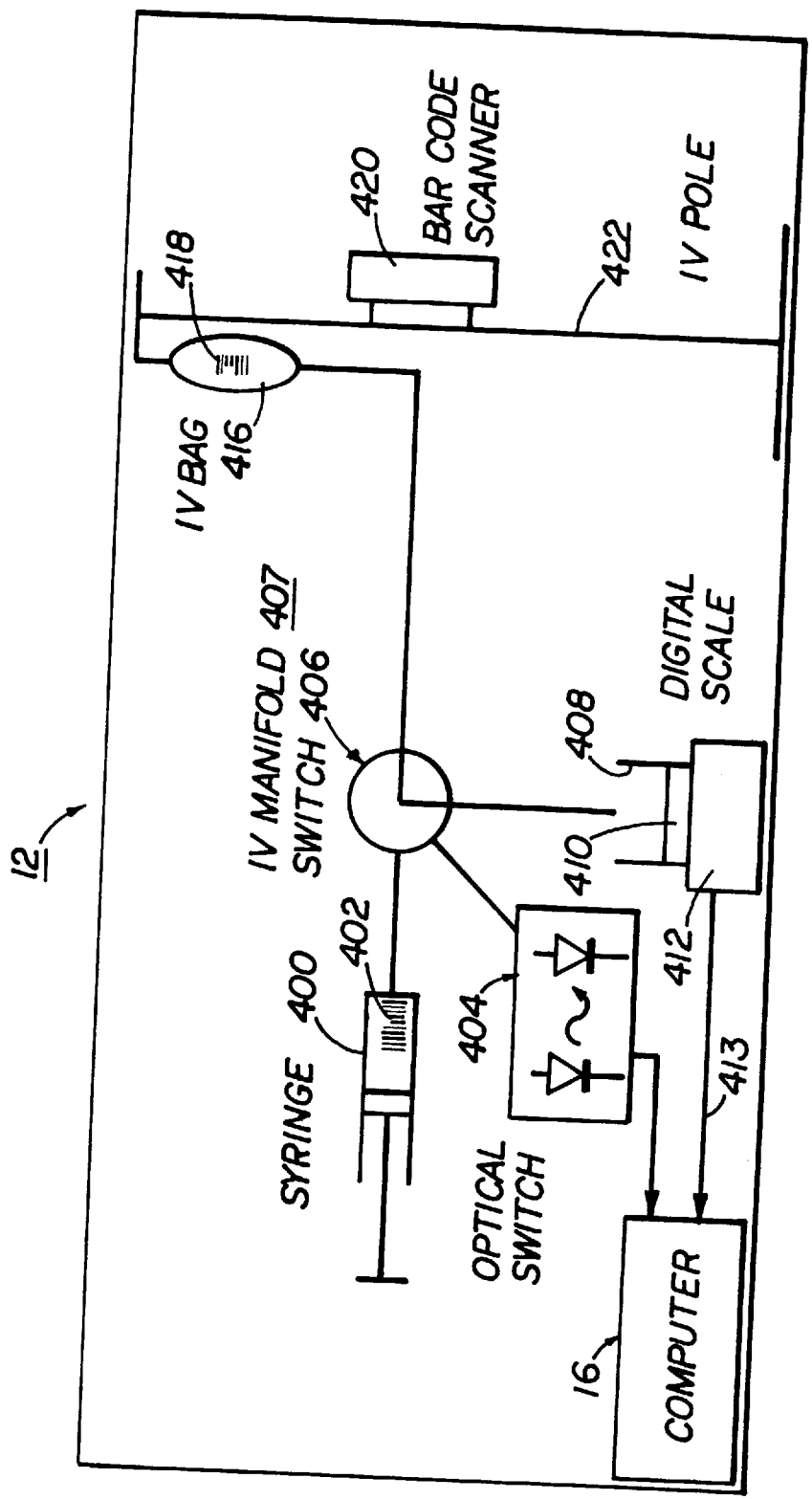
FIG. 5 is schematic view of a system for detection, identification and quantification of drug and fluid administered to the patient simulator.

Referring now to FIG. 5, an apparatus and associated system 12 is provided wherein each syringe 400 and each IV bag 416 has a unique bar code label (402 and 418, respectively) that identifies the, drug or IV fluid (including whole blood) as well as the concentration contained therein. Furthermore, there is conveniently mounted a bar code scanner 420 on an IV pole 422 (or some other convenient, fairly proximal item) next to the head 50 of the manikin 4. The trainee is instructed to scan either the syringe 400 or the IV bag 416 by the bar code scanner 420 (Metrologic MS941) mounted on the IV pole 422 before administering the drug (which could be an intravenous anesthetic) or IV fluid. If the trainee should turn on the IV manifold switch 406 (Baxter, Chicago, Ill.) prior to the scanning in of a drug identity, then a small warning beep is emitted (not shown) to remind the trainee to use the bar code scanner 420.

An optical emitter/detector pair (the optical switch) 404 (Motorola, Inc.) is situated so as to transmit to the computer 16 an input/output signal indicating the physical status of the IV manifold switch 406, i.e. on or off. Thus, the system is able to determine whether the input of medicament or fluid is being routed from the syringe 400 or the IV drip bag 416.

The present invention discloses a method of detecting and identifying a drug administered in real time in an integrated patient simulator during simulated medical surgery using a manikin. The method requires the trainee to scan a bar code 402 or 418 affixed to an implement which may be either an intravenous drip bag 416 or a syringe 400, wherein the respective bar code indicates the type and concentration of drug contained within the implement. It should be noted that any means of containing a drug and delivering it to the patient simulator 1 could be used with the bar code system described herein. Next, a bar code scanner 420 is used to scan the bar code. The scanner 420 is connected to the computer 16 such that the bar code which was scanned can be translated into computer usable information about the drug so detected and identified.

Thus, the detection and identification of drug and IV fluid administration is automatically performed, enhancing the realism of the simulation. The system is also made more robust because an instructor who may be distracted is no longer required for the drug identification.

EXAMPLE V

Drug and IV Fluid Quantification

FIG. 5 also shows a means for drug and IV fluid quantification. In a preferred embodiment, it is desirable to achieve a measurement accuracy of ±0.25 ml for drugs injected via a syringe 400. An IV manifold 407 is provided so that fluid can flow either from an IV bag 416 or from a syringe 400. A switch 406 must be manually turned on to select a fluid inlet to be connected to the intravenous needle (not shown) in the manikin 4. The switch 406 was equipped with an optical emitter-detector pair 404 mounted on its underside (out of view of the user) which transmits a signal to the module 38 detailing the position of the IV manifold switch 406 at all times. The light path between the emitter detector pair 404 is interrupted when the switch is turned to inject drug via the syringe 400. An interruption of the light beam causes an input/output (I/O) bit to change state on the microcontroller board (one of the single-board computers on the star-network 501).

As it is administered by the trainee, the IV fluid or drug 410 is emptied into a bucket 408 placed on a digital scale 412 (Denver Instruments, D1-5K, Arvada, Colo.). The digital scale 412 used herein contains a serial port (not shown) for outputting information along cable 413 to module 38 (not shown) to a computer 16 or other electronic device. The weight on the digital scale at the moment switch 406 is turned on is recorded by a computer in module 38 polling the serial port on the scale 412. When the switch 406 is turned back to its original position after the drug in the syringe 400 has been injected, the bit connected to the emitter-detector pair 404 again changes state. The initial weight read by the scale when the IV manifold switch 406 is turned on is subtracted from the new weight on the scale 412. The weight difference can be used to determine the volume and thus the amount of drug injected from the syringe 400 because the concentration is known from the bar code 402 or 418 label on the syringe 400 or IV bag 416.

Furthermore, by polling the digital scale 412 at known time intervals when the IV manifold switch 406 is in the IV drip position, the rate of IV fluid administration can be calculated by dividing the change in weight over a given time interval by the time interval. The type of IV fluid administered (Ringer's lactate, saline, etc.) will already have been identified by the bar code scanner 420 as described in Example IV.

Thus, there is disclosed a method of quantifying the amount of a drug or IV fluid administered in real time in an integrated patient simulator during simulated medical surgery using a manikin 4. This method requires that the initial weight of a reservoir 408 first be determined. This reservoir 408 should be capable of containing a suitable volume of drug administered. In addition, the reservoir 408 need not be emptied after each application of a drug, but instead, the weight of the fluid in the reservoir may be used to determine when the reservoir 408 is almost full. Thus, the initial weight of the reservoir 408 may include an amount of drug 410 already contained therein. This is obviated by the use of a drip bag 416, where, over time, the reservoir 408 will fill and thus the initial weight for determining the amount administered during the relevant time period will be ever increasing.

An initial weight is determined from the digital scale 412. Next, a drug is delivered to the reservoir 408. In the present embodiment, the delivery is accomplished by diverting drug flow from the implement chosen, e.g., the syringe 400 via the manifold 407 to the reservoir via a conduit (not shown) or some other means. After the occurrence of a preselected event, a second weight is determined by polling the digital scale 412. This polling may be initiated by the computer in module 38 which is connected via a serial link to the scale 412 so that the reading may be transmitted to the computer 16 for processing. The preselected event may be that a certain amount of time has passed, or that the trainee has finished administering an injection. To determine the actual weight of drug administered, it is simply necessary for the computer 16 to subtract the initial weight from the second weight. Based on the difference value so computed, the patient simulator 1 then determines via the computer 16 a simulated response according to a time- and event-based script, a computer model or a combination of a time- and event-based script and a computer model based on the physiological state of the patient simulator 1. A skilled artisan would appreciate that a syringe and an IV drip bag are not the exclusive implements useful for practicing the invention.

Also disclosed in conjunction with this method is an apparatus for quantifying the amount of a drug administered in real time in an integrated patient simulator during simulated medical surgery.

EXAMPLE VI

Star Network for Distributed Processing

Figure 6:
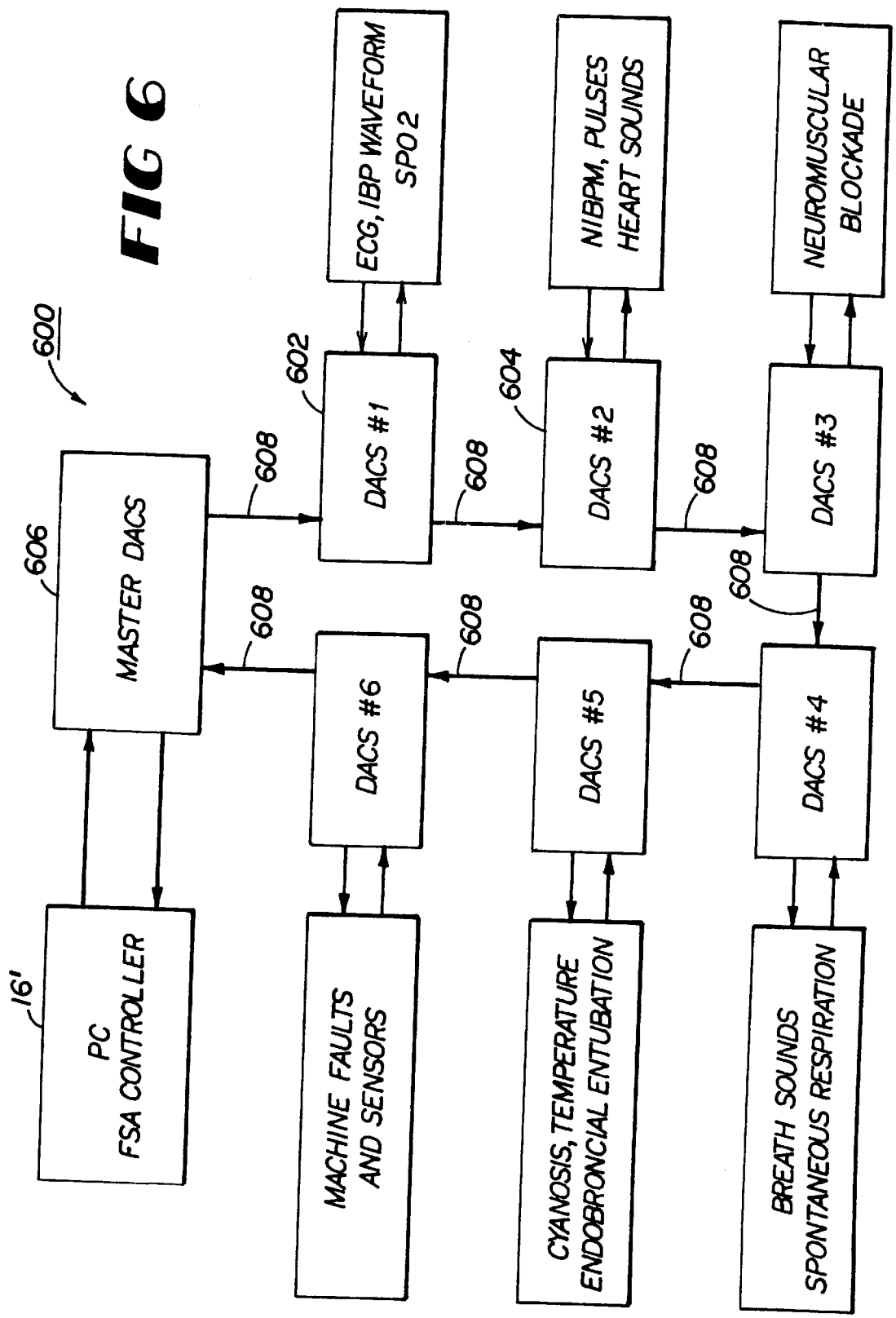
FIG. 6 is a schematic of the ring configuration distributed processing network of the present invention.

Referring to FIGS. 6 and 7, a star network is used as the distributed processing network of the instant invention. The star network 501 of single board computers is implemented via a computer 16 and a multiplexer 20, using an RS-232 serial interface protocol. Distributed processing allows the parallel processing of different tasks. The inherent robustness of the star network makes the simulation less vulnerable to failure of any of the single-board computers 506, 514, . . . on the network (unlike in a ring configuration as depicted in FIG. 6).

It is instructive to first examine a ring network 600 as shown in FIG. 6. In FIG. 6, a computer 16 is used to drive a master microcontroller board 606. A signal is first sent out via line 608 to a first single board computer 602. That computer 602 determines whether it needs to handle the signal or not. In addition, the signal is allowed to pass along path 608 to the next computer 604. In this manner, a serial circuit is traversed by the signal using pathways 608. If any one of the computers, e.g. 602 or 604 fails, then the entire network 600 will fail.

The use of a star network 501 as depicted in FIG. 7 overcomes this significant problem. It is instructive to examine the flow of the electric cardiac synchronization pulse 500 along the star network 501. First, the computer 16 generates the pulse 500. The pulse is converted via a digital to analog converter card 502 into an analog signal 504. This signal is transmitted along a cable to the backplane 516 of the star network 501. There, the signal is in effect transmitted to each single board computer, e.g. 508, in parallel via junctures 506, 514, . . . synchronizing all cardiac related events.

The single board computer, e.g. 508, has two-way communications via line 510. Finally, the multiplexer 20 has two-way communication also with the computer 16 via line 512. In sharp contrast, however, to the ring network 600 of FIG. 6, if one of the single board computers, e.g. 508, happens to fall, a signal such as a cardiac pulse signal 500 will not be rendered undeliverable to the other single board computers due to an open circuit such as in a serially configured ring network 600. Instead, the malfunctioning unit will simply not contribute to the patient simulator system 1.

EXAMPLE VII

Triggering Scheme for Cardiac Rhythm Related Events

The current invention also provides a triggering scheme for cardiac rhythm related events. This scheme consists of a synchronization pulse 500. See FIG. 7. Within the software physiological model 520 programmed into the computer 16 (a first programmed computing means) that drives the patient simulator 1, there is an ECG waveform generator 518. The ECG waveform generator 518 outputs the frequency and pattern of the ECG. The ECG waveform generator also outputs the synchronizing pulse 500 via a D/A converter 502 that gets delivered to all computers, e.g. 508 (a second programmed computing means), on the star network 501 that require the electric cardiac rhythm synchronizing pulse 500. Thus, both arrhythmias and normal sinus rhythms are instantly simulated and displayed on the appropriate subsystems and monitors.

A time offset to allow for travel time or lag of the cardiac pulse through the body can be added at the local single board computer level, e.g. board 508. For example, in a real patient, the cardiac pulse will appear sooner at sites closer to the heart, e.g., the carotid pulse, compared to sites further from the heart, e.g., the radial pulse. Thus, although the carotid and radial pulse will be at the same frequencies and exhibit the same arrhythmias, the simulated pulses can be made staggered in time by adjusting a time delay at the local board level, e.g. 508.

Thus, there is disclosed a method of synchronizing cardiac rhythm related events in real time In an integrated simulator during simulated medical procedures using a manikin. The method requires the transmitting throughout a distributed processing network 501 or 600 associated with the integrated patient simulator 1. As noted above, it is preferable if the distributed processing network is a star network 501.

Using this method, it is thus possible to actuate various subsystem devices associated with the manikin 4 such as radial pulses. The radial pulse, because of its distance from the heart, can be delayed as dictated by the software model operating on the relevant single-board computer, e.g., 508.

Also provided is an apparatus for synchronizing output devices related to a cardiac rhythm in real time in an integrated patient simulator during simulated medical surgery. This apparatus uses a manikin 4 with at least one output device. At least one electric cardiac rhythm synchronizing pulse 500 is distributed over the distributed processing network 501 as described supra. It is preferable that the distributed processing network is a star network 501.

EXAMPLE VIII

Simulation of Lung and Heart Sounds

Similarly, the lung sounds associated with a certain lung field should be at that specific lung field in area 52 of the manikin 4 and not another location. Further, depending on the physiological condition of the patient being simulated, the sounds will be either normal or wheezing. Various other sounds, such as sounds indicating abnormal physiologic states, may also be simulated.

To accomplish simulation of lung and heart sounds, it is advantageous to store various different banks of sounds of breathing on analog memory integrated circuits. In the preferred embodiment, ISD 1016AP integrated circuit chips (Information Storage Devices, Inc., San Jose, Calif.) are used to effect the simulation of various sounds. These chips possess Direct Analog Storage Capability (DAST), whereby the information from an analog input source is stored directly into and read directly from standard electrically erasable programmable read only memory (EEPROM). DAST (capable of storing signals of up to 230 distinct voltage levels) allows storage of up to eight times the information per cell compared to digital solutions (allowing for only two voltage states, i.e. a bit is either on or off). Since EEPROM is non-volatile, no battery back-up is required to preserve recorded information and overall power consumption is significantly reduced. Thus, EEPROM are particularly suitable to remote or portable embodiments.

Within the ISD 1016AP integrated circuit, filters, preamplifiers, automatic gain control and speaker drivers have been included in a single chip. Thus, the ISD 1016AP used in the instant patient simulator is a complete single-chip solution. Thus, only a microphone, speaker and a power supply are needed to create a complete record/playback system.

When the appropriate triggering signal is transmitted to the appropriate chip, the analog signal encoded therein is played to the appropriate speaker located in the vicinity of area 52 of the manikin 4. Most sounds for the present invention are cyclical (e.g., heart beat), or biphasic (e.g. inspiration and expiration sounds of breathing) in nature thus lending themselves to DAST chip suitability.

Figure 9:
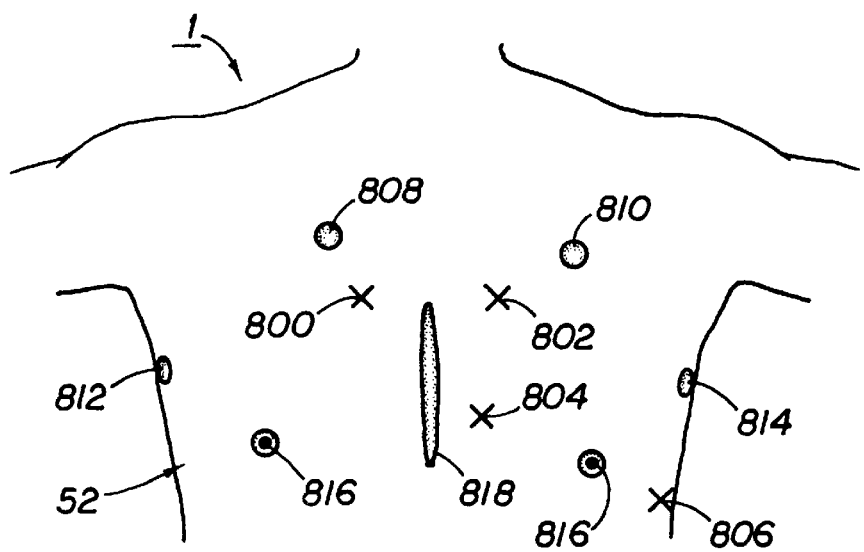
FIG. 9 is a schematic showing the placement of speakers for emitting heart and lung sounds.
Figure 10:
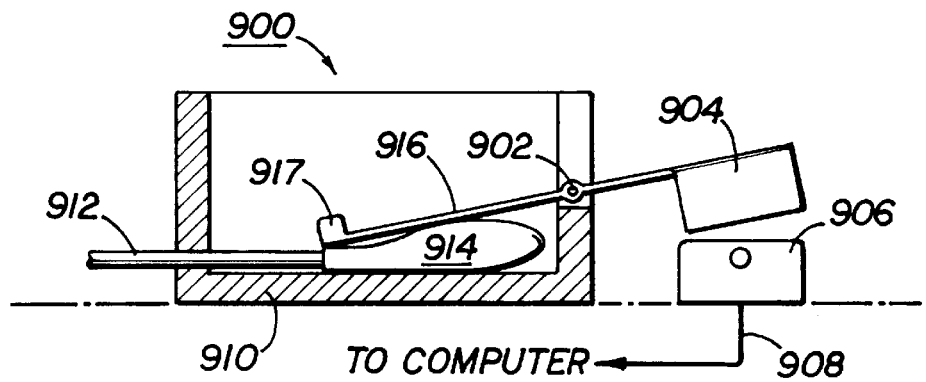
FIG. 10 is a cut-away perspective view of an apparatus for detecting the inflation of a pulmonary artery catheter balloon where the balloon is un-inflated.
Figure 11:
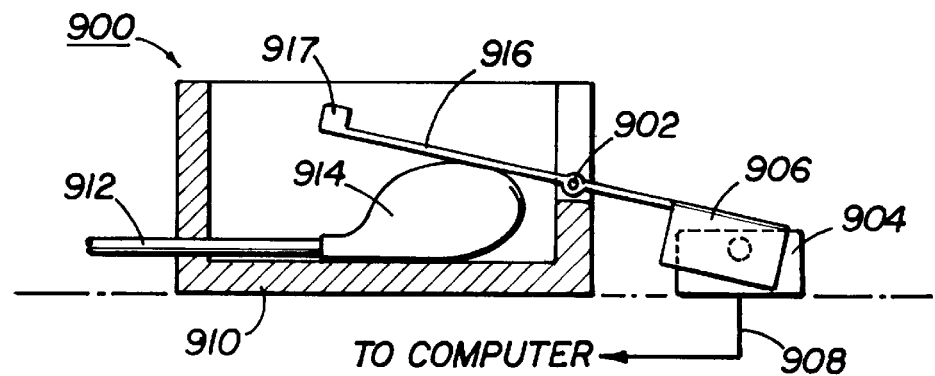
FIG. 11 is a cut-away perspective view of an apparatus for detecting the inflation of a pulmonary artery catheter balloon where the balloon is inflated.

Referring now to FIG. 9, which encompasses area 52 of manikin 4, heart sound speakers are located at the right upper sternal border 800, left upper sternal border 802, left lower sternal border 840 and the apex 806. In addition, speakers for outputting lung sounds are located at the right apex 808, the left apex 810, the right lateral 812 and left lateral 814 positions. A subcutaneous simulated sternum 818 and nipples 816 are indicated for reference.

In addition, the sounds heard over the lung fields 52 are different according to respiratory phase, i.e. inhalation or expiration. Thus, proper synchronization of lung sounds produced by the DAST chips is necessary to avoid negative reinforcement due to the incorrect sound being omitted (e.g., expiratory sounds while inhaling).

The first derivative with respect to time of each lung volume obtained by excursion sensor 118 is calculated to determine the phase of the respiratory cycle. The second derivative is used to detect the transition from inspiration to expiration and vice versa, which transition occurs at a time when the second derivative of lung volume with respect to time is zero. The ECG respiratory pattern (generated in the ECG signal generator 518) of the present patient simulator 1 is influenced by the respiratory pattern and phase and the physiological model 520. The actual movement of the bellows 100 triggers the production of appropriate lung sounds.

In order to simulate sounds (heart, lung, esophageal, bowel, etc.) in the correct locations, an array of small speakers (not shown) is distributed below the skin of the manikin 4 at the appropriate locations (near area 52). The appropriate sounds are supplied to appropriate locations under the control of a triggering scheme dictated by the control computer 16.

Furthermore, changes in sound are used to reflect abnormal physiological conditions. Auscultation has been traditionally used to diagnose the condition of a patient and forms a significant portion of the training of medical students. Thus, septal and valvular defects in the heart may be detected by listening for certain sounds associated with these conditions.

In the present patient simulator, sounds associated with abnormal physiological conditions (e.g., heart valve defects) are stored and when appropriately triggered are sent to the proper location (speaker) on the manikin 4.

Breathing sounds may also be simulated. Thus, the current invention contemplates a method of simulating sounds of breathing in real time in an integrated patient simulator 1 during simulated medical procedures using a manikin 4, comprising the steps of continuously determining the volume (via an excursion sensor 118, for example) of at least one bellows 100 associated with the manikin 4. Using standard mathematical procedures based on the time and the volume determined, it is then necessary to calculate a first derivative of the bellows volume over time to determine the phase of the respiratory cycle. Furthermore, by calculating a second derivative of the bellows volume over time, it is possible to determine a transition in phase of the respiratory cycle (e.g. inhalation to exhalation or vice versa). Based upon the first and second derivatives of the bellows volume over time, a sound is output or directed to and through a sound outputting means, such as a speaker located at an appropriate place, e.g. the mouth of the manikin 4. The sound may be an audible sound of breathing corresponding to an appropriate physiological sound.

In addition, based upon the physiological state of the patient simulator 1, it is possible to determine whether an abnormal condition exists. If so, then the patient simulator 1 will alter the audible sounds of breathing corresponding to the appropriate physiological sound based upon the abnormal condition effecting the physiological state.

To accomplish these methods, a related apparatus for simulating sounds of breathing in real time in an integrated patient simulator during simulated medical procedures is also disclosed. The relevant physiological sounds are prerecorded onto the analog chips described above. The outputting means is similar to that detailed supra.

In addition to sounds of breathing, heart and lung (or lung field) sounds are also disclosed by the current invention. Thus, there is disclosed a method of simulating heart sounds in real time in an integrated patient simulator during simulated medical procedures using a manikin. At an appropriate time, duration and frequency, a sound outputting means is activated which emits an audible heart sound or lung sound to the pertinent speaker corresponding to an appropriate physiological sound output location (see FIG. 9). As in the simulation of sounds of breathing, the method also contemplates a step of determining whether an abnormal condition is effecting the physiological state and, if so, altering the audible heart or lung sound corresponding to the appropriate physiological sound based upon the abnormal condition effecting the physiological state. This alteration may occur through any appropriate means including a programmed computing means such as a computer 16. Breathing sounds may also be similarly altered.

To accomplish these tasks, the current invention includes an apparatus for simulating heart and lung sounds in real time in an integrated patient simulator during simulated medical procedures. The device has been described more fully supra.

EXAMPLE IX

Simulation of Continuous Blood Gases

Modern clinicians now have available a device which allows nearly continuous monitoring of blood gases ($pO_2$, $pCO_2$, pH, temperature) through an in-dwelling probe placed in the artery of a patient.

The instant patient simulator is capable of emulating the behavior of this new device. Using a physiological model of the cardiovascular and pulmonary systems, the appropriate readings can be artificially generated depending on the state of the patient simulator system 1. These outputs are channeled through a serial port to the display panel of a mock-up of a continuous blood gas analysis device (not shown). Thus, a real-time continuous display of blood gases is available as another realistic source of information for the trainee to react to. The device thus allows the student to see the interaction between the invasive blood gas analysis and other parameters obtained non-invasively, e.g. pulse oximetry.

Thus, the present invention discloses a method of simulating the monitoring of continuous blood gases in real time in an integrated patient simulator during simulated medical procedures using a manikin. The simulation requires the knowledge of the current arterial blood as values generated by the physiological model. The information about the state will include such items as simulated blood pH, temperature, and arterial $O_2$ and arterial $CO_2$ partial pressures. Based upon the physiological state being simulated, the physiological model will determine the above appropriate blood gas information. With this information, the computer 16 will actuate a mock continuous blood gas machine (not shown) according to the appropriate blood gas information.

To accomplish this simulation, the current invention discloses an apparatus for simulating the determination of continuous blood gases in real time in an integrated patient simulator during simulated medical procedures. The apparatus comprises a manikin 4 interconnected with a mock continuous blood gas machine (not shown). The mock blood gas machine is actuated via electronic signals from the computer 16 depending upon the physiological state and model. Thus the mock blood gas machine has a means for simulating an output. Thus, the display panel is under the control of the computer 16 of the patient simulator 1. There is also a means, preferably a cable, for delivering a signal to the mock blood gas machine in order to create a simulated output in real time.

EXAMPLE X

PA Catheter Inflation Detection

The pulmonary arteries (PA) catheter is used to measure these patient parameters related to cardial performance, pulmonary artery pressure (systolic, diastolic, and mean), pulmonary artery occlusion ("wedge") pressure (left ventricular end diastolic pressure LVEDP, an indicator of left ventricular filling) and cardiac output.

The PA catheter is introduced via the jugular vein (near the neck) or the subclavian vein into the superior vena cava, through the right atrium, right ventricle and into the pulmonary artery. When the PA catheter balloon is not inflated, the PA catheter measures systolic and diastolic PA pressure. When the balloon is inflated, the drag on the balloon from the blood "floats" the balloon downstream into the pulmonary capillary bed where it gets "wedged" as the PA diameter narrows down. The pressure measured after the balloon is inflated is called the wedge pressure which very closely approximates the LVEDP in most patients. Therefore, after the student on the simulator inflates the PA catheter balloon, a change in the PA pressure trace is expected within 1 to 10 seconds.

The present invention provides an apparatus 900 for determining the inflation of a pulmonary artery catheter balloon 914 in real time in an integrated patient simulator during simulated medical procedures. The apparatus has a housing 910 defining a catheter receiving cavity therein. A lever 916 is pivotally mounted on a pivot 902 on the housing 910. The lever has a first end 917 and a second end 904 where the first end 917 is movable in response to the inflation of the balloon 914.

Also included is a means 906 for detecting the position of the second end 904 whereby when the balloon 914 is inflated a signal 908 is generated by the detecting means 906 to indicate the inflation.

This signal 908 is used by the programmed computing means in calculating the appropriate physiological response to whether the PA catheter tip 912 and the balloon 914 attached thereto has been inflated.

EXAMPLE XI

Difficult Airway

Figure 8:
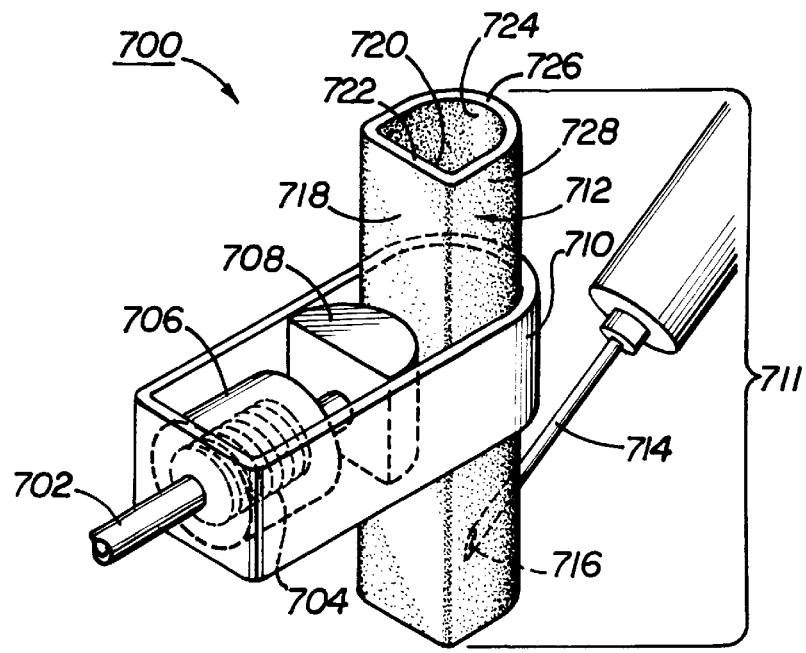
FIG. 8 is a perspective view of the means for simulating a difficult airway.

Referring now to FIG. 8, there is shown a means for simulating a difficult airway 700 on the patient simulator 1. The means for simulating a difficult airway 700 provides a method of demonstrating the effects of certain kinds of reactions, such as allergic, wherein the trachea (a flexible airway) constricts. If an ETT tube cannot be inserted into the trachea before complete constriction, the patient is not able to breath, obviously resulting in a serious condition. The clinical solution is to perform an emergency cricothyrotomy which entails puncturing a hole in the front of the trachea so that air may flow below the point of constriction and into the lungs.

The means for simulating the difficult airway 700 of the instant invention entails modifications to the head 50 of the manikin 4. The modified head 50 uses an approximately 1" diameter hose or conduit 712 attached to the neck portion. The shape of this conduit 712 is "D" shaped with the flat portion of the "D" 722 aligned with what would be the back of the neck. A horseshoe shaped holding clamp 710 is fitted over the exterior surface of the semicircular wall of the "D" 726. Upon the proper actuation of a pneumatic actuator line 702, a pneumatic cylinder 706 forces a plunger 708 into contact with the linear portion of the "D" 722. Enough force is transmitted to completely occlude the airway 711 thus resulting In a difficult airway. Upon removal of the actuation signal, the pneumatic cylinder 706 discontinues forcing the plunger 708 forward and the spring return 704 retracts the plunger 708.

The trainee faced with a difficult airway situation must perform a cricothyrotomy. To do so, the trainee uses a traecheastomy kit 714 to puncture a hole into the trachea at an appropriate location. On the instant patient simulator 1, the puncture is made in a replaceable membrane 716 (NAFCO, location Texas).

More specifically, the difficult airway system 700 is an apparatus which sits in the neck of the head 50 of the manikin 4. Thus, if the instructor chooses to simulate a difficult airway, then a means for constricting, crushing or sealing a flexible airway 711 in the neck of the manikin 4 is actuated.

In the preferred embodiment, flexible airway 711 comprises a conduit 712 having a flat back wall 722 having opposed, parallel sides therealong and an interior surface 720 and an opposed exterior surface 718. The airway 711 also has a semicircular front wall 726 which has edges connected to respective sides of the flat back wall 722. Wall 726 also has an interior surface 724 and an exterior surface 728. In addition, there is a plunger 708 disposed adjacent to the exterior surface 718 of the flat back wall 722. To effect a difficult airway, there is also a means for actuating the plunger 708 (for stance, the means could be a pneumatic cylinder 706 activating the plunger 708 capable of forcibly crushing or sealing the flexible airway 711 with a spring return 704 for retracing the plunger), whereby the plunger 708 engages the exterior surface 718 of the flat back wall 722 so as to move the interior surface 720 of the flat back wall 722 a selected distance toward the interior surface 724 of the semicircular front wall 726. This motion thus crushes or seals the flexible airway 711 upon sufficient movement of the plunger 708. In a preferred embodiment, the plunger 708 is complimentarily shaped to the interior surface 724 of the semicircular wall 726. Thus, the present invention discloses a method of simulating a difficult airway 700 in real time.

EXAMPLE XII

Gas Exchange With Mass Flow Controller

Referring mainly to FIG. 2, it is desirable to create realistic simulated uptake and delivery of respiratory gases such as oxygen, carbon dioxide, nitrous oxide and nitrogen along with the volatile and anesthetic gases in the mechanical lung 26. The present invention uses gas substitution to implement this function. With gas substitution, a constant amount of gas is removed from the lung and its composition analyzed in real time by a gas analyzer 48. For each gas, uptake and delivery is modeled by permitting an appropriate inflow of that gas (through conduit 102 and into the bellows 100).

Thus, for example with oxygen, the oxygen inflow rate may be calculated as equal to the oxygen fraction times the outflow rate minus the desired oxygen uptake measured in liters per minute. Thus, continuously controllable mass flow controllers 122 were used to create the required inflow rates of nitrogen, oxygen, nitrous oxide and carbon dioxide.

The vane pump 106 of the present invention creates an outflow rate which depends upon the bellows 100 pressure. The outflow rate for the particular implementation described herein is:

outflow rate=3+0.032 times the bellows pressure.

This value is substituted in the oxygen inflow rate formula of the physiological model to compensate for the increase in oxygen outflow through the vane pump 106. The bellows pressure is measured by pressure sensors 101.

The continuous flow rates allowable by the MFC's 122 give rise to more precise, smoother adjustment of gas composition in the bellows 100, thereby reducing the pressure fluctuations associated with other techniques. Pressure compensation avoids unrealistic readings as would result with pulmonary pressures applied during routine ventilation in anesthesia.

EXAMPLE XIV

Simulation of Non-linear Compliances

The ability to control lung compliance by computer without manual intervention is desirable because a real patient sometimes undergoes changes in compliance during anesthesia, e.g., during thoracic surgery when the surgeon opens the chest cavity. The patient simulator of the present invention provides a means for simulating compliance curves which are non-linear, i.e. sigmoidal in nature and thus more realistic.

The purpose of the mechanical lung 26 aspect of the patient simulator is to reproduce the airway pressure-flow characteristics and gas composition of the natural lung in normal and pathophysiologic conditions arising during anesthesia. One important aspect of the pressure-flow characteristic is compliance. Static compliance is defined as the increase of lung volume divided by the increase in pressure used to create that increased volume. Existing lung models implement compliance with springs and/or compressible gas chambers. That type of modeling makes computer control over compliance cumbersome. In the instant patient simulator, compliance is a variable in the controlling computer and can be rapidly changed via computer.

The lung volumes are realized by mechanical bellows 100. The volume of the bellows 100 is derived from the excursion sensor 118 attached to each of the two bellows 100 (although, as previously noted, only one is shown). Based on the excursions, respective lung volumes are computed. The double acting pneumatic piston 112 (one for each lung) then creates a volume dependent downward force on the bellows 100 due to a differential in pressure from the EPR 108 versus the MPR 110 that is equivalent to the computer 16 force that would be opposing inflation due to the lung compliance.

The means for accomplishing non-linear compliances is trough the use of the double acting piston 112. One side of the piston is exposed to a bias pressure from a manual pressure regulator (MPR) 110 while the other side of the piston is exposed to a pressure from an electronic pressure regulator (EPR) 108. The EPR 108 is computer controlled via a digital-to-analog (D/A) line (not shown). The D/A line is supplied with the muscle pressure signal described elsewhere herein. Thus, in addition to normal lung activities and compliances, a cough may be simulated by suddenly lowering the pressure of the EPR 108 below that of the bias pressure of the MPR 110.

Thus, the present invention discloses a method of simulating non-linear compliances in real time in an integrated patient simulator 1 during simulated medical procedures using a manikin 4. The method includes the step of first computing the volume of at least one bellows 100. Volume is preferably determined via the excursion sensor 118 output described elsewhere herein. Based on the volume reading and optionally a reading from the pressure sensors 101 situated in the lung the compliances may be modeled. The modeling itself is embodied in the use of a bellows actuating means which has a first constant pressure from an MPR 110 and a second variable pressure from an EPR 108 acting on respective sides of a double acting piston 112 capable of actuating the bellows 100 whereby varying the second variable pressure causes the bellows 100 to exhibit the desired compliance force on the bellows 100 according a time- and event-based script, a computer model or a combination of a time- and event-based script and a computer model based on the physiological state of the patient simulator 1.

In generating a compliance, the volume measured by the excursion sensor 118 is used as one input in a predetermined mathematical compliance formula dictated by the physiological model. The output of the mathematical compliance formula is the desired or target lung pressure.

What is claimed is:

1. An apparatus for synchronizing output devices related to a cardiac rhythm in real time in an integrated patient simulator during simulated medical surgery, comprising:
   a. a manikin;
   b. at least one output device associated with the manikin;
   c. a first programmed computing means capable of generating at least one electric cardiac rhythm synchronizing pulse;
   d. a distributed processing network connected to said first programmed computing means and said at least one output device for transmitting said at least one electric cardiac rhythm synchronizing pulse; and
   e. a second programmed computing means connected to said distributed processing network for calculating a simulated response to the at least one cardiac rhythm synchronizing pulse and for actuating via the distributed processing network the at least one output device associated with the manikin in real time.

2. The apparatus of claim 1, wherein the distributed processing network is a star network.

3. The apparatus of claim 1, wherein the at least one output device emulates a radial pulse in the manikin.

4. The apparatus of claim 3, wherein said second programmed computing means introduces a time delay in the at least one cardiac rhythm synchronizing pulse to emulate the radial pulse in said manikin.

5. The apparatus of claim 4, wherein a second output device emulates a carotid pulse in the manikin, and wherein the time delay introduced by said second programmed computing means causes the radial pulse emulated in the manikin to occur after the carotid pulse emulated in the manikin, and at an identical frequency as the carotid pulse.

6. The apparatus of claim 5, wherein the carotid pulse and the radial pulse emulated in the manikin exhibit identical simulated arrhythmias.

7. The apparatus of claim 1, wherein the simulated response is calculated by said second programmed computing means according to a time-and-event-based script, a computer model or a combination of a time-and-event-based script and a computer model based on a physiological state of said integrated patient simulator.

8. A method of synchronizing cardiac rhythm related events in real time in an integrated simulator during simulated medical procedures using a manikin, comprising the steps of:
   a. generating at least one electric pulse, corresponding to a cardiac rhythm synchronizing pulse, in a first programmed computing means;
   b. transmitting throughout a distributed processing network associated with the integrated patient simulator the at least one electric pulse to a second programmed computing means;
   c. processing the at least one electric pulse in said second programmed computing means; and
   d. generating a response in at least one output device associated with the manikin based on the processed electric pulse.

9. The method of claim 8, wherein the distributed processing network is a star network.

10. The method of claim 8, wherein the step of generating a response in at least one output device comprises emulating a radial pulse in the manikin.

11. The method of claim 10, wherein said processing step comprises introducing a time delay in the cardiac rhythm synchronizing pulse to emulate the radial pulse in said manikin.

12. The method of claim 11, further comprising emulating a carotid pulse in a second output device associated with the manikin, and wherein the time delay introduced in said processing step causes the radial pulse emulated in the manikin to occur after the carotid pulse emulated in the manikin, and at an identical frequency as the carotid pulse.

13. The method of claim 12, wherein the carotid pulse and the radial pulse are emulated in the manikin to exhibit identical simulated arrhythmias.

14. The method of claim 8, wherein said processing step comprises calculating a simulated response to the at least one electric pulse based on a time-and-event-based script, a computer model or a combination of a time-and-event-based script and a computer model based on a physiological state of said integrated patient simulator.

15. An apparatus for actuating an output device related to a cardiac rhythm in real time in an integrated patient simulator, comprising:

a. a manikin having an output device associated therewith;
   b. a first programmed computing means capable of generating a cardiac rhythm synchronizing pulse;
   c. a second programmed computing means for receiving the cardiac rhythm synchronizing pulse and generating a simulated response thereto; and
   d. a distributed processing network for communicating the cardiac rhythm synchronizing pulse between said first programmed computing means and said second programmed computing means, and for communicating the simulated response between said second programmed computing means and the output device.

16. The apparatus of claim 15, wherein said distributed processing network is a star network.

17. The apparatus of claim 15, wherein the output device emulates a radial pulse in said manikin.

18. The apparatus of claim 17, wherein said second programmed computing means introduces a time delay in the cardiac rhythm synchronizing pulse to emulate the radial pulse in said manikin.

19. The apparatus of claim 18, further comprising a second output device which emulates a carotid pulse in the manikin, and wherein the time delay introduced by said second programmed computing means causes the radial pulse emulated in the manikin to occur after the carotid pulse emulated in the manikin, and at an identical frequency as the carotid pulse.

20. The apparatus of claim 19, wherein the carotid pulse and the radial pulse emulated in the manikin exhibit identical simulated arrhythmias.

21. The apparatus of claim 15, wherein the simulated response is calculated by said second programmed computing means according to a time-and-event-based script, a computer model or a combination of a time-and-event-based script and a computer model based on a physiological state of said integrated patient simulator.

* * * * *